US006562836B1

United States Patent
Szarek et al.

(10) Patent No.: US 6,562,836 B1
(45) Date of Patent: May 13, 2003

(54) METHODS AND COMPOUNDS FOR INHIBITING AMYLOID DEPOSITS

(75) Inventors: Walter A. Szarek, Kingston (CA); Donald F. Weaver, Kingston (CA); Xianqi Kong, Dollard-des-Ormeaux (CA); Ajay Gupta, Pointe-Claire (CA); David Migneault, Laval (CA)

(73) Assignee: Queen's University of Kingston, Kingston (CA)

( * ) Notice: Subject to any disclaimer, the term of this patent is extended or adjusted under 35 U.S.C. 154(b) by 0 days.

(21) Appl. No.: 09/576,677

(22) Filed: May 23, 2000

Related U.S. Application Data

(60) Provisional application No. 60/143,123, filed on Jul. 9, 1999, and provisional application No. 60/135,545, filed on May 24, 1999.

(51) Int. Cl.[7] .................. A61K 31/44; A61K 31/47
(52) U.S. Cl. ............... 514/307; 514/308; 514/311; 514/313; 514/314
(58) Field of Search .................. 514/311, 313, 514/314, 307

(56) References Cited

U.S. PATENT DOCUMENTS

| | | | |
|---|---|---|---|
| 3,872,125 A | 3/1975 | Houlihan et al. | 260/283 |
| 4,199,601 A | 4/1980 | Durlach | 424/315 |
| 4,267,194 A | 5/1981 | Durlach | 424/315 |
| 4,271,189 A | 6/1981 | Durlach | 424/315 |
| 4,355,043 A | 10/1982 | Durlach | 424/289 |
| 4,386,081 A | 5/1983 | Helgstrand et al. | 424/212 |
| 4,522,811 A | 6/1985 | Eppstein et al. | 514/2 |
| 4,540,564 A | 9/1985 | Bodor | 424/9 |
| 4,563,470 A | 1/1986 | Durlach | 514/347 |
| 4,591,583 A | 5/1986 | Helgstrand et al. | 514/120 |
| 5,164,295 A | 11/1992 | Kisilevsky et al. | 435/7.8 |
| 5,166,320 A | 11/1992 | Wu et al. | 530/395 |
| 5,194,654 A | 3/1993 | Hostetler et al. | 558/152 |
| 5,242,932 A | 9/1993 | Gandy et al. | 514/313 |
| 5,276,059 A | 1/1994 | Caughey et al. | 514/647 |
| 5,374,548 A | 12/1994 | Caras | 424/450 |
| 5,385,915 A | 1/1995 | Buxbaum et al. | 514/313 |
| 5,389,623 A | 2/1995 | Bodor | 514/169 |
| 5,399,331 A | 3/1995 | Loughrey et al. | 424/450 |
| 5,416,016 A | 5/1995 | Low et al. | 435/240.1 |
| 5,463,092 A | 10/1995 | Hostetler et al. | 554/40 |
| 5,728,375 A | 3/1998 | Kisilevsky et al. | 424/78.31 |
| 5,840,294 A | 11/1998 | Kisilevsky et al. | 424/78.31 |
| 5,869,469 A | 2/1999 | Szarek et al. | 514/120 |
| 5,952,389 A | 9/1999 | Fogel | 514/665 |
| 6,037,327 A | * 3/2000 | Castillo et al. | 514/23 |

FOREIGN PATENT DOCUMENTS

| | | |
|---|---|---|
| CA | 2031433 | 6/1991 |
| CA | 2046037 | 1/1992 |
| DE | 43 13 118 A1 | 10/1994 |
| EP | 003275 | 9/1981 |
| EP | 115 657 | 8/1984 |
| EP | 236 251 | 9/1987 |
| EP | 797 992 | 10/1997 |
| WO | WO 92/14456 | 9/1992 |
| WO | WO 94/22437 | 10/1994 |
| WO | WO 94/27602 | 12/1994 |
| WO | WO 95/06477 | 3/1995 |
| WO | WO 96/28187 | 9/1996 |
| WO | WO 96/37612 | 11/1996 |
| WO | WO 97/07402 | 2/1997 |
| WO | WO 97/09976 | 3/1997 |
| WO | WO 97/16191 | 5/1997 |
| WO | WO 98/11923 | 3/1998 |
| WO | WO 98/13046 | 4/1998 |
| WO | WO 98/25938 | 6/1998 |
| WO | WO 00/06133 | 2/2000 |
| WO | WO 00/57707 | 10/2000 |
| WO | WO 00/64420 | 11/2000 |
| WO | WO 01/03680 | 1/2001 |

OTHER PUBLICATIONS

Aprile, C. et al., "Cardiac and pleuropulmonary AL amyloid imaging with technetium–99m labelled aprotinin," *Eur. J. Nucl. Med.*, 22(12):1393–1401 (1995).

Axelrad et al., "Further Characterization of Amyloid Enhancing Factor", *Laboratory Investigation*, 47:139–146 (1982).

Baures PW, et al. Discovering transthyretin amyloid fibril inhibitors by limited screening. Bioorg Med Chem. Aug. 1998;6(8):1389–401.

Boismare, F. et al., "A Homotaurine Derivative Reduces the Voluntary Intake of Ethanol by Rats: are Cerebral GABA Receptors Involved?" *Pharmacology Biochemistry & Behavior*, (1984), vol. 21, pp. 787–789.

Briggs, A.D. et al., "Acyloxymethyl and 4–acyloxybenzyl diester prodrugs of phosphonoformate," *Tetrahedron*, 52(47):14937–14950 (1996).

Brissette et al., "Differential Induction of the Serum Amyloid A Gene Family in Response to an Inflammatory Agent and to Amyloid–enhancing Factor", *The Journal of Biological Chemistry*, 264(32):19327–19332 (1989).

Campagna, Francesco et al., "Cyclic Amidine Analogues Of Taurine And Homotaurine: Systhesis And Effects On Rats Skeletal Muscle." *IL FARMACO*, (1994), vol. 49, No. 10, pp. 653–658.

(List continued on next page.)

*Primary Examiner*—Zohreh Fay
*Assistant Examiner*—Brian-Yong S. Kwon
(74) *Attorney, Agent, or Firm*—Lahive & Cockfield, LLP; Elizabeth A. Hanley, Esq.; Theodore R. West, Esq.

(57) ABSTRACT

Methods and compositions which are useful in the treatment of amyloidosis. In particular, methods and compositions are provided for inhibiting, preventing and treating amyloid deposition, e.g., in pancreatic islets, wherein the amyloidotic deposits are islet amyloid polypeptide (IAPP)-associated amyloid deposition or deposits. The methods of the invention involve administering to a subject a therapeutic compound which inhibits IAPP-associated amyloid deposits. Accordingly, the compositions and methods of the invention are useful for inhibiting IAPP-associated amyloidosis in disorders in which such amyloid deposition occurs, such as diabetes.

172 Claims, 14 Drawing Sheets

OTHER PUBLICATIONS

Caughey, B. et al., "Sulfated Polyanion Inhibition of Scrapie–Associated PrP Accumulation in Cultured Cells", *Journal of Virology,* 67(2):643–650 (1993).

Caughey, B., "Scrapie–Associated PrP Accumulation and Its Prevention: Insights from Cell Culture", *Brit. Med. Bull.,* 49:860–872 (1993).

Caughey, B., "Protease–resistant PrP accumulation and scrapie agent replication: a role for sulphated glycosaminoglycans? ", *Biochem. Soc. Trans.,* 22:163–167 (1994).

Caughey, "Scrapie–associated PrP accumulation and agent replication: effects of sulphated glycosaminoglycan analogues", *Phil. Trans. R. Soc. Lond.* B, 343:399–404 (1994).

Caughey, B. et al., "Binding of the Protease–Sensitive Form of Prion Protein PrP to Sulfated Glysocaminoglycan and Congo Red", *Journal of Virology,* 68:2135–2141 (1994).

Chabenat, C. et al., "Physicochemical, Pharmacological and Pharmacokinetic Study of New GABAergic Compound, Calcuim Acetylhomotaurinate." *Meth and Find Exptl Clin Pharmacol,* (1988); vol. 10, No. 5, pp.: 311–317.

Dow et al., "Effects of 4–deoxy–L–threo–pentose, a novel carbohydrate, on neural cell proteoglycan synthesis and function", *Biochimica et Biophysica Acta,* 1156:7–14 (1992).

Drug Evaluations: Acamprosate; *Micromedex*, (1974–1997), vol. 91, Expiration Date: Feb. 28, 1997.

Durbin, P. H. et al., "Evidence Of Acamprosate Penetration Into The Rat Brain." *ehavioural Pharmacology,* (1995), vol. 6, p.: 620.

Ehlers et al., "Dextran Sulphate 500 Delays and Prevents Mouse Scrapie by Impairment of Agent Replication in Spleen", *J. Gen. Virol.,* 65:1325–1330 (1984).

Fraser, P.E. et al., "Fibril formation by primate, rodent, and Dutch–hemorrhagic analogues of Alzheimer amyloid beta–protein,"*Biochem.,* 31(44):10716–10723 (1992).

Fraser et al., "Effects of Sulfate Ions on ALzheimer–beta/A4 Peptide Assemblies—Implications for Amyloid Fibril–Proteoglycan Interactions", *J. Neurochem.,* 59:1531–1540 (1992).

Fujii, Akira et al., et al., "Probiotics. Antistaphylococcal and Antifibrinolytic Activites of ω–Amino– and ω–Guanidinoalkanesulfonic Acids." *Journal of Medicinal Chemistry,* (1975), vol. 18, No. 5, pp.: 502–505.

Georgiev, V. S. et al., "Drug–induced modifications of the immune response. 1. Substitute 1–phenylisoquinolines" J. Med. Chem., 22(4), pp.: 348–352 (1979).

Gorin et al., "A novel esterification procedure applied to synthesis of biologically active esters of foscarnet," *Tet. Lett.,* 38(6):2791–2794 (1997).

Girault, J. et al., "Determination of calcium acetylhomotaurinate in human plasma and urine by combined gas chromatography–negative–ion chemical ionization mass spectrometry." *J. Chromatogr B Biomed Appl.,* (1990), vol. 530, No. 2, pp.: 295–305.

Grant, K. A. et al., "Reinforcing and Discriminative Stimulus Effects of Ca–Acetyl Homotaurine in Animals." *Pharmacology Biochemistry & Behavior,* (1988) vol. 32, pp.: 607–611.

Hawkins, P.N., "Diagnosis and monitoring of amyloidosis," *Baillieres Clin. Rheumatol.,* 8(3):635–659 (1994).

Kagan, D.Z. and Rozinova, V.N. "Inhibition of amyloidosis with Congo Red in experimental amyloidosis", *Problemy Tuberkuleza,* 40:72–74 (with English translation) (1974).

Kisilevsky et al., "A Critical Analysis of Postulated Pathogenetic Mechanisms in Amyloidogenesis", *Critical Reviews in Clinical Laboratory Sciences,* 29(1):59–82 (1992).

Kisilevsky, R. et al., "Arresting amyloidosis in vivo using small–molecule anionic sulphonates or sulphates: implications for Alzheimer's disease", *Nature Med.* 1:143–148 (1995).

Kisilevsky, "From arthritis to Alzheimer's disease: current concepts on the pathogenesis of amyloidosis", *Can. J. Physiol. Pharmacol.,* 65:1805–1815 (1987).

Kisilevsky, "Theme and Variations on a String of Amyloid", *Neurobiology of Aging,* 10:499–500 (1989).

Kisilevsky, et al. "The Potential Significance of Sulphated Glycosaminoglycans as a Common Constituent of all Amyloids", *Medical Hypotheses,* 26:231–236 (1988).

Kisilevsky, "Heparan Sulfate Proteoglycans in Amyloidogenesis: An Epiphenomenon, A Unique Factor, or the Tip of a More Fundamental Process?", *Laboratory Investigation,* 63(5):589–591 (1990).

Leveugle, B. et al., "Binding of heparan sulfate glycosaminoglycan to β–amyloid peptide: inhibition by potentially therapeutic polysulfated compounds", *NeuroReport,* 5:1389–1392 (1994).

Lhuintre, Jean–Pierre et al., "Ability of Calcium Bis Acetyl Homotaurine, A Gaba Agonist, To Prevent Relapse In Weaned Alcholics." *The Lancet,* (1985), vol. 1(8436), pp.: 1014–1016.

Lyon et al., "Co–deposition of Basement Membrane Components during the Induction of murine Splenic AA Amyloid", *Laboratory Investigation,* 64(6):785–790 (1991).

Malmusi L. et al., "1,2,3,4–Tetrahydroisoquinoline and Related Analogs of The Phenylalkylamine Designer Drug MDMA", Medicinal Chemistry Research, Birkhaeuser, Boston, U.S., vol. 6(6), pp. 412–426 (1996).

Narindrasorasak et al., "High Affinity Interactions between the Alzheimer's β–Amyloid Precursor Proteins and the Basement Membrane Form of Heparan Sulfate Proteoglycan", *The Journal of Biological Chemistry,* 266(20):12878–12883 (1991).

Narindrasorasak et al., "Characterization of High Affinity Binding between Laminin and Alzheimer's Disease Amyloid Precursor Proteins", *Laboratory Investigation,* 67(5):643–652 (1992).

Silverman, R.B. "The organic chemistry of drug design and drug action," Academic Press, chp. 8, (1992).

Small et al., "Association and Release of the Amyloid Protein Precursor of Alzheimer's Disease from Chick Brain Extracellular Matrix", *J. Neuroscience,* 12:4143–4150 (1992).

Snow, A. D. and Kisilevsky R., "Temporal Relationship between Glycosaminoglycan Accumulation and Amyloid Deposition during Experimental Amyloidosis", *Laboratory Investigation,* 53(1):37–43 (1985).

Snow, AD et al., "Characterization of tissue and plasma glycosaminoglycans during experimental AA amyloidosis and acute inflammation. Qualitative and quantitative analysis," *Lab. Invest.* 56(6):665–75 (1987).

Snow AD, et al. "Sulfated glycosaminoglycans: a common constituent of all amyloids?" *Lab. Invest.* 56(1):120–3 (1987).

Snow et al., "Sulfated Glycosaminoglycans in Alzheimer's Disease", *Human Pathology*, 18(5):506–510 (1987).

Snow et al., "A Close Ultrastructural Relationship between Sulfated Proteoglycans and AA Amyloid Fibrils", *Laboratory Investigation*, 57(6):687–697 (1987).

Snow et al., "Sulfated glycosaminoglycans in amyloid plaques of prion diseases", *Acta Neuropathol.*, 77:337–342 (1989).

Snow et al., "A Temporal and Ultrastructural Relationship Between Heparan Sulfate Proteoglycans and AA Amyloid in Experimental Amyloidosis", *The Journal of Histochemistry and Cytochemistry*, 39(10):1321–1330 (1991).

Tape et al., "Direct Evidence for Circulating apoSAA as the Precursor of Tissue AA Amyloid Deposits", *Scand. J. Immunol.*, 28:317–324 (1988).

Travis, "New Piece in Alzheimer's Puzzle", *Science*, 261:828–829 (1993).

Wong et al., "Influence of Sulphate ions on the Structure of AA Amyloid Fibrils", *Scand J. Immunol.*, 32:225–232 (1990).

Young et al., "The ultrastructural localization of sulfated proteoglycans is identical in the amyloids of Alzheimer's disease and AA, AL, senile cardiac and medullary carcinoma–associated amyloidosis", *Acta Neuropathol.*, 78:202–209 (1989).

Young et al., "Localization of the Basement Membrane Heparan Sulfate Proteoglycan in Islet Amyloid Deposits in Type II Diabetes Mellitus", *Arch. Pathol. Lab. Med.*, 116:951–954 (1992).

Lacoste, Anne–Marie et al. "Inhibition of D–Alanyl–D–Alanine Ligase in Different Bacterial Species by Amino Phosphonic Acids" *Current Microbiol.* 2(2):113–117 (1979).

Masuda et al. "Effect of taurine on non–specific protection against bacterial infection" Database STN International, Chemical Abstracts Service, Accession No. 105:108004 (1985) (Abstract only).

O'Brien, et al. "Human Islet Amyloid Polypeptide Expression in Cos–1 Cells a Model of Intracellular Amyloidgenesis" *American Journal of Pathology* 147(3): 609–616 (Sep. 1995).

Powell, et al. "Insulin and Polyionic Sulphonates Modify Human Islet Amyloid Polypeptide Fibril Aggregation in Vitro" *Diabetologia* 41:656 (Aug. 1998).

Westermark, "Islet Pathology of Non–Insulin–Dependent Diabetes Mellitus (NIDDM)" *Diabet. Med.* 13:S46–8 (Sep. 1996).

U.S. patent application Ser. No. 09/560,505, Szarek et al., filed Apr. 2000.

* cited by examiner

3-[2-(1,2,3,4-Tetrahydroisoquinolinyl)]-1-propanesulfonic acid

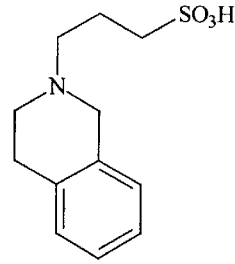

3-[2-(6,7-Dimethoxy-1,2,3,4-tetrahydroisoquinolinyl)]-1-propanesulfonic acid

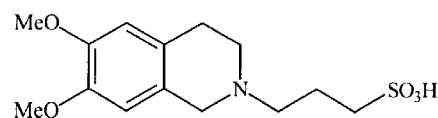

3-[2-(6-Methoxy-1,2,3,4-tetrahydro-isoquinolinyl)]-1-propanesulfonic acid

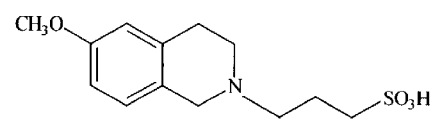

2-(2-Sulfobenzoyl)-1,2,3,4-tetrahydroisoquinoline, sodium salt

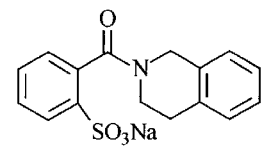

2-(2-Sulfobenzyl)-1,2,3,4-tetrahydroisoquinoline, sodium salt

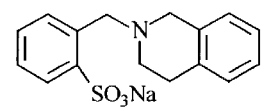

1,2,3,4-Tetrahydroisoquinoline, hydrochloride

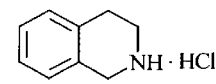

3-[2-(3-Carboxy-1,2,3,4-tetrahydroisoquinolinyl)]-1-propanesulfonic acid, disodium salt

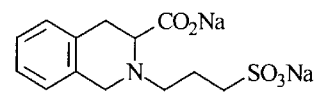

*N*-Methyl-*N*-phenyl-3-[2-(1,2,3,4-tetrahydroisoquinolinyl)]-1-propanesulfonamide

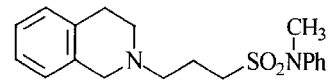

4-[2-(1,2,3,4-Tetrahydroisoquinolinyl)]-1-butanesulfonic acid, sodium salt

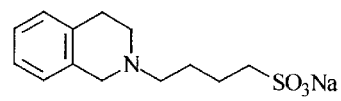

FIG. 1

4-[2-(6,7-Dimethoxy-1,2,3,4-tetrahydroisoquinolinyl)]-1-butanesulfonic acid

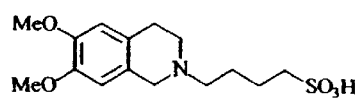

4-[2-(6-methoxy-1,2,3,4-tetrahydroisoquinolinyl)]-1-butanesulfonic acid

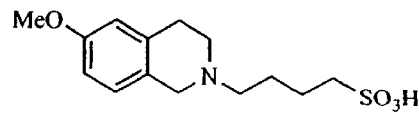

3-[2-(1,2,3,4-Tetrahydroisoquinolinyl)]-1-propylthiophosphonic acid, disodium salt

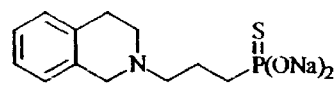

3-[2-(6-Methoxy-1,2,3,4-tetrahydroisoquinolinyl)]-1-propanesulfonic acid, sodium salt

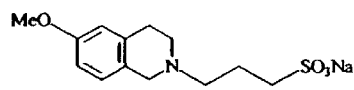

3-[2-(8-Methoxy-1,2,3,4-tetrahydroisoquinolinyl)]-1-propanesulfonic acid, sodium salt

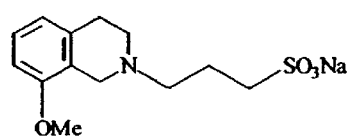

1,2,3,4-Tetrahydro-8-isoquinolinesulfonic acid

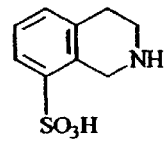

3-[2-(6-Dimethylamino-1,2,3,4-tetrahydroisoquinolinyl)]-1-propanesulfonic acid, sodium salt

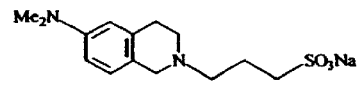

3-[2-(6-Chloro-1,2,3,4-tetrahydroisoquinolinyl)]-1-propanesulfonic acid, sodium salt -

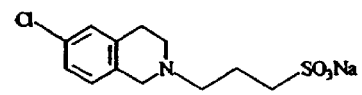

4-[2-(1,2,3,4-Tetrahydroisoquinolinyl)]-1-butanesulfonic acid

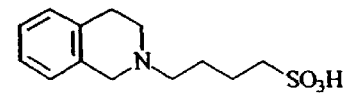

1,2,3,4-Tetrahydro-5-isoquinolinesulfonic acid

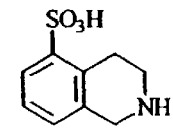

FIG. 2

1-Sulfopropyl-2-[2-(1,2,3,4-tetrahydroisoquinolinyl)methyl]-4,5-dihydroimidazole

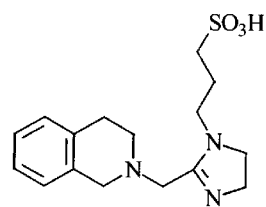

3-[7-Methoxy-2-(1,2,3,4-tetrahydro-isoquinolinyl)]propylphosphonic acid, disodium salt

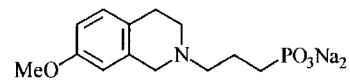

3-[6-Methoxy-2-(1,2,3,4-tetrahydro-isoquinolinyl)]propylphosphonic acid, disodium salt

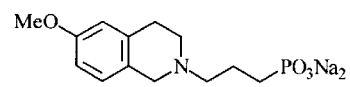

3-[8-Methoxy-2-(1,2,3,4-tetrahydro-isoquinolinyl)]propylphosphonic acid, disodium salt

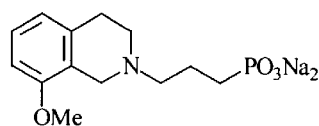

3-[2-(3-Methoxycarbonyl-1,2,3,4-tetrahydroisoquinolinyl)]propylphosphonic acid, disodium salt

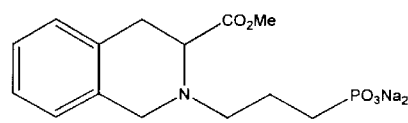

3-[6-Methoxy-2-(1,2,3,4-tetrahydro-isoquinolinyl)]propylphosphonic acid, diethyl ester

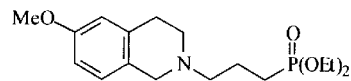

3-[7-Methoxy-2-(1,2,3,4-tetrahydro-isoquinolinyl)]propylphosphonic acid, diethyl ester

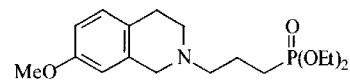

N-Phosphonoacetyl-6-methoxy-1,2,3,4-tetrahydroisoquinoline, disodium salt

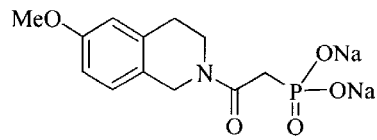

6-Methoxy-1,2,3,4-tetrahydroisoquinoline, hydrochloride

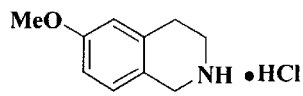

N-Sulfoacetyl-1,2,3,4-tetrahydroisoquinoline, sodium salt

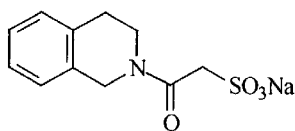

FIG. 3

N-Ethyl-1,2,3,4-tetrahydroisoquinoline, hydrochloride 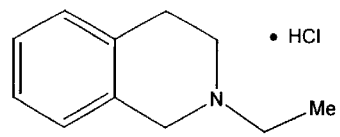

N-Propyl-1,2,3,4-tetrahydroisoquinoline, hydrochloride 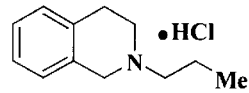

N-Propyl-6-methoxy-1,2,3,4-tetrahydroisoquinoline, hydrochloride 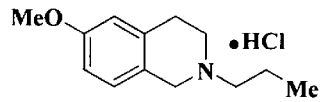

5-[(1,2,3,4-Tetrahydroisoquinol-2-yl)methyl]isoxazol-3-ol 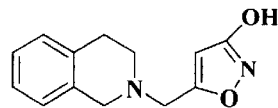

5-[(6-Methoxy-1,2,3,4-tetrahydroisoquinol-2-yl)methyl]isoxazol-3-ol 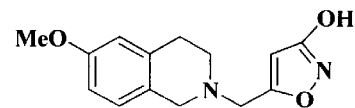

(±)-Laudanosoline hydrobromide trihydrate 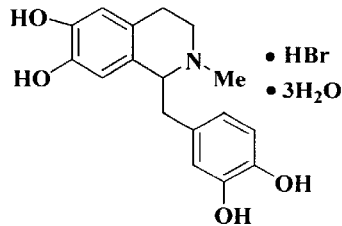

(-)-1-[5-Chloro-2-(methylamino)phenyl]-1,2,3,4-tetrahydroisoquinoline (-)-tartrate 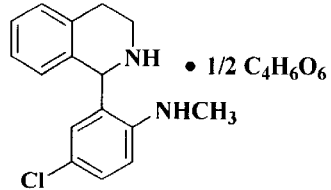

(S)-(-)-1,2,3,4-Tetrahydro-3-isoquiolinecarboxylic acid 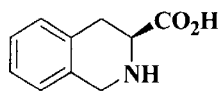

Tetrahydropapaveroline hydrobromide (Norlaudanosoline hydrobromide) 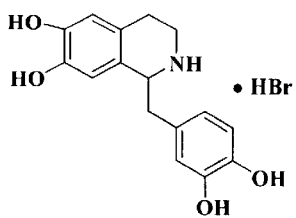

FIG. 4

3-phenyl-5-[2-(1,2,3,4-tetrahydroisoquinolyl)methyl]isoxazole

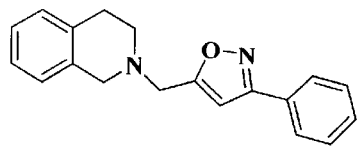

3-Methyl-5-[2-(1,2,3,4-tetrahydroisoquinolyl)methyl]isoxazole

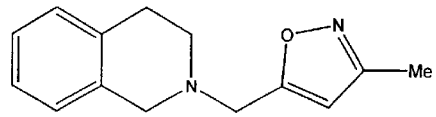

5-[2-(1,2,3,4-Tetrahydroisoquinolyl)methyl]isoxazole-3-carboxylic acid

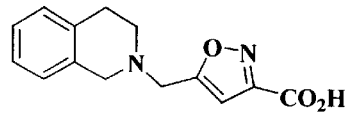

5-phenyl-3-[2-(1,2,3,4-tetrahydroisoquinolinyl)methyl]isoxazole

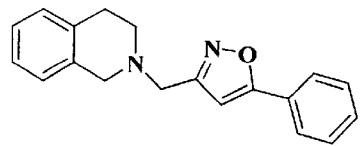

3-[2-(1,2,3,4-Tetrahydroisoquinolyl)methyl]isoxazole-5-carboxylic acid

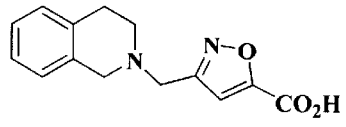

(2S)-2-Amino-2-[3-(2-1,2,3,4-tetrahydroisoquinolylmethyl)isoxazol-5-yl]acetic acid

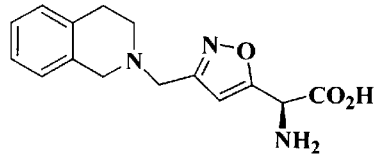

3-[2-(1,2,3,4-Tetrahydroisoquinolyl)-methyl]isoxazole-5-L-alanine

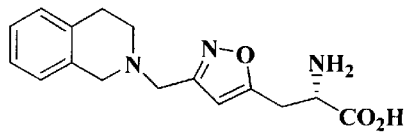

4-[2-(1,2,3,4-Tetrahydroisoquinolyl)methyl]-L-phenylalanine

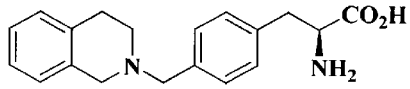

5-[2-(1,2,3,4-Tetrahydroisoquinolyl)methyl)-1H-1,2,3,4-tetrazole

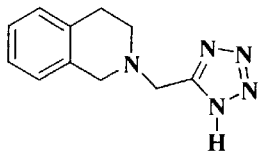

FIG. 5

5-(1,2,3,4-Tetrahydroisoquinol-6-yl)-1*H*-1,2,3,4-tetrazole 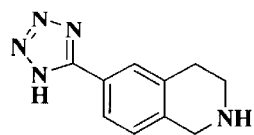

5-[6-(1,2,3,4-Tetrahydroisoquinolyl)methyl]-1*H*-1,2,3,4-tetrazole 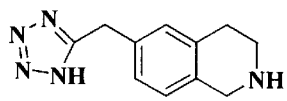

5-{2-[6-(1,2,3,4-Tetrahydroisoquinolyl)]ethyl}-1*H*-1,2,3,4-tetrazole 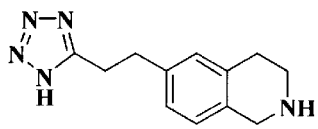

5-(1,2,3,4-Tetrahydroisoquinol-7-yl)-1*H*-1,2,3,4-tetrazole 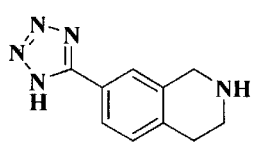

5-[7-(1,2,3,4-Tetrahydroisoquinolyl)methyl]-1*H*-1,2,3,4-tetrazole 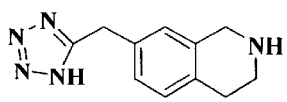

5-{2-[7-(1,2,3,4-Tetrahydroisoquinolyl)]ethyl}-1*H*-1,2,3,4-tetrazole 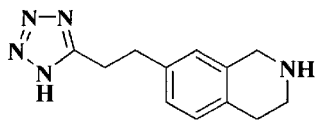

6-Methoxy-1,2,3,4-tetrahydroisoquinoline 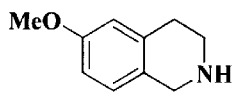

7-Methoxy-1,2,3,4-tetrahydroisoquinoline 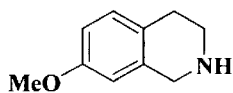

6,7-Dimethoxy-1,2,3,4-tetrahydroisoquinoline 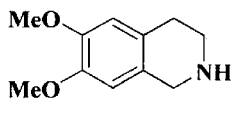

1,2,3,4-Tetrahydroisoquinoline-6-carbonitrile 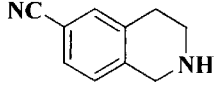

1,2,3,4-tetrahydroisoquinoline-7-carbonitrile 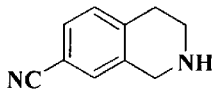

FIG. 6

6-Amino-1,2,3,4-tetrahydroisoquinoline 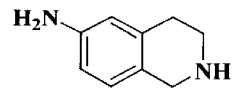

7-Amino-1,2,3,4-tetrahydroisoquinoline 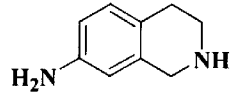

7-(3,4,5-Trimethoxybenzoyl)amino-1,2,3,4-tetrahydroisoquinoline 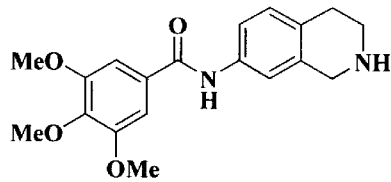

7-β-D-Glucopyranosyl-6-methoxy-1,2,3,4-tetrahydroisoquinoline 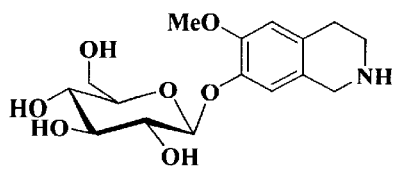

6-β-D-Glucopyranosyl-7-methoxy-1,2,3,4-tetrahydroisoquinoline 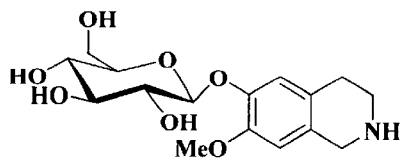

(1,2,3,4-Tetrahydroisoquinol-1-yl)phosphonic acid 

5,6,7,8-Tetrahydro-2*H*-1,3-dioxoleno[4,5-*g*]isoquinoline 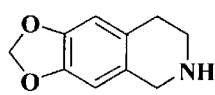

1,2,3,4-Tetrahydrobenzo[*g*]isoquinoline 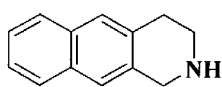

(1,2,3,4-Tetrahydroisoquinol-7-ylsulfonyl)aminobenzene 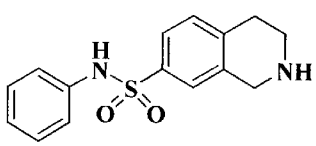

FIG. 7

1-[(1,2,3,4-Tetrahydroisoquinol-7-ylsulfonyl)amino]-3,4-dichlorobenzene 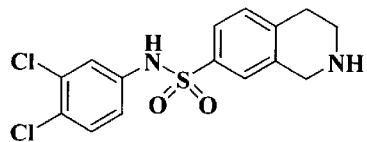

7-(2,2,2-Trifluoroacetyl)-1,2,3,4-tetrahydroisoquinoline 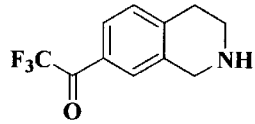

7-Benzyl-1,2,3,4-tetrahydroisoquinoline 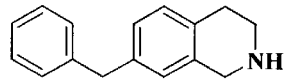

7-Benzoyl-1,2,3,4-tetrahydroisoquinoline 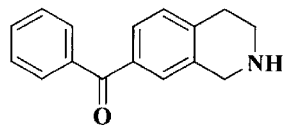

7-Acetyl-1,2,3,4-tetrahydroisoquinoline 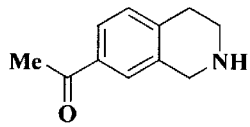

1,2,3,4-Tetrahydroisoquinoline-7-carboxylic acid 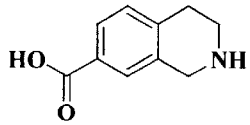

1,2,3,4-Tetrahydroisoquinoline-7-carboxamide 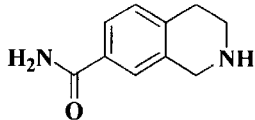

7-Aminomethyl-1,2,3,4-tetrahydroisoquinoline 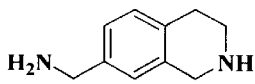

7-hydroxymethyl-1,2,3,4-tetrahydroisoquinoline 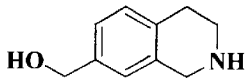

7-Methyl-1,2,3,4-tetrahydroisoquinoline 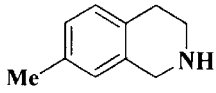

7-hydroxy-1,2,3,4-tetrahydroisoquinoline 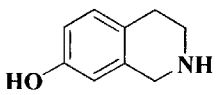

FIG. 8

7-(Methanesulfonyl)amino-1,2,3,4-
tetrahydroisoquinoline
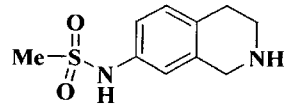
7-(Methanesulfonyl)aminomethyl-1,2,3,4-
tetrahydroisoquinoline
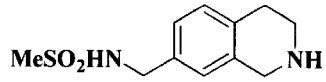
7-Nitro-1,2,3,4-tetrahydroisoquinoline
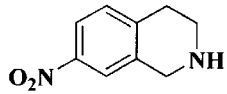
1,2,3,4-Tetrahydroisoquinoline-7-sulfonamide
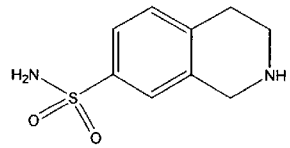
7-Trifluoromethyl-1,2,3,4-tetrahydroisoquinoline
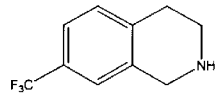
7-Methylthio-1,2,3,4-tetrahydroisoquinoline
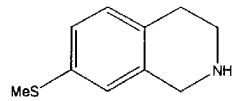
FIG. 9

8-hydroxy-5-quinolinesulfonic acid
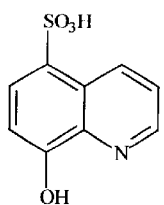
8-hydroxy-7-iodo-5-quinolinesulfonic acid
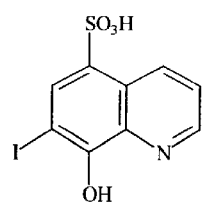
5-Chloro-8-quinolylmethylsulfonic acid, sodium salt
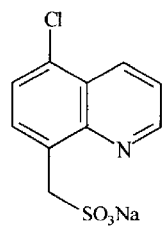
5,8-Dibromo-6-quinolylmethylsulfonic acid, sodium salt
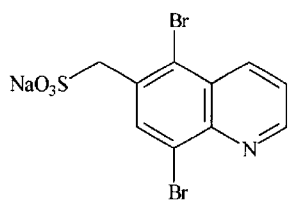
8-Ethoxy-5-quinolinesulfonic acid, sodium salt
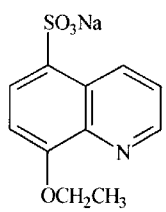
5-Chloro-6-quinolylmethylsulfonic acid, sodium salt
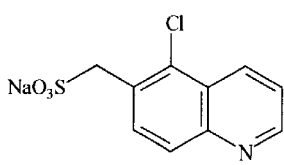
Quinoline yellow
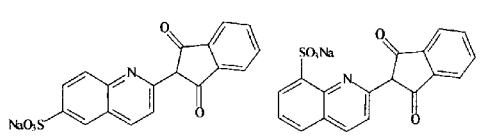
5-Bromo-6-quinolylmethylsulfonic acid, sodium salt
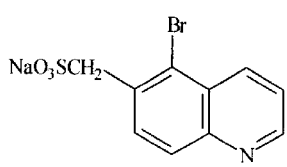
FIG. 10

7-Bromo-8-hydroxy-5-quinolinesulfonic acid 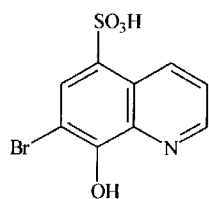
7-Chloro-8-hydroxy-5-quinolinesulfonic acid 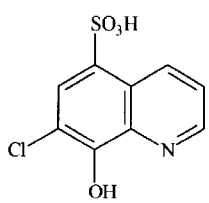
5-Chloro-8-hydroxy-7-quinolinesulfonic acid 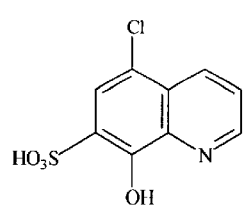
5-Bromo-8-hydroxy-7-quinolinesulfonic acid 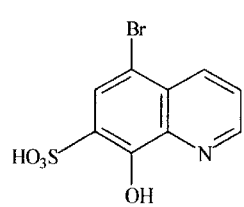
8-hydroxy-2-methyl-5-quinolinesulfonic acid 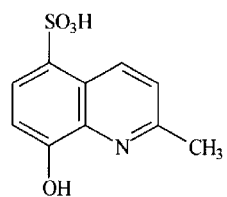
8-hydroxy-2-methyl-5,7-quinolinedisulfonic acid 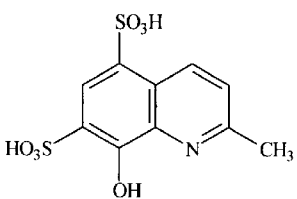
5-Chloro-8-hydroxy-2-methyl-7-quinolinesulfonic acid 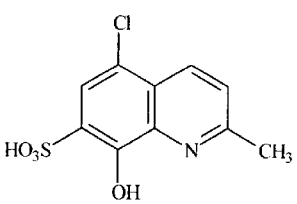
FIG. 11

5-Bromo-8-hydroxy-2-methyl-7-quinolinesulfonic acid
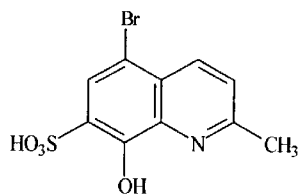
2,6-Quinolyldimethyldisulfonic acid, disodium salt
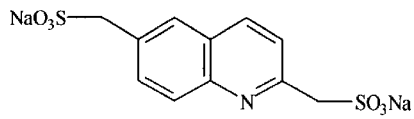
5-Chloro-2,6-quinolyldimethyldisulfonic acid, disodium salt
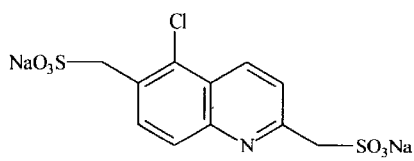
8-methoxy-5-quinolinesulfonic acid, sodium salt
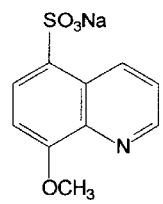
8-Methoxy-5-[N-(2-N',N'-diethylethylamino)]quinolinesulfonamide
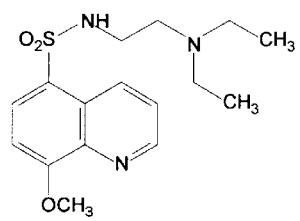
8-Methoxy-5-[N-(2-N',N'-indolineethylamino)]quinolinesulfonamide
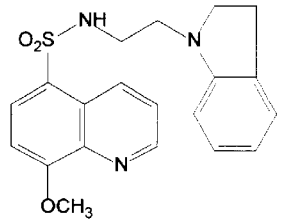
FIG. 12

| | |
|---|---|
| Cyclohexylsulfamic acid, sodium salt | 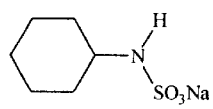 |
| 2-hydroxyethylsulfamic acid sulfate, disodium salt | NaO$_3$SNHCH$_2$CH$_2$OSO$_3$Na |
| 3-hydroxypropylsulfamic acid sulfate, disodium salt | NaO$_3$SNHCH$_2$CH$_2$CH$_2$OSO$_3$Na |
| N,N-Bis(2-hydroxyethyl)sulfamic acid disulfate, disodium salt | NaO$_3$SN(CH$_2$CH$_2$OSO$_3$Na)$_2$ |
| 3-[2-(1,2,3,4,5,6,7,8-Octahydroisoquinolinyl)]-1-propanesulfonic acid | 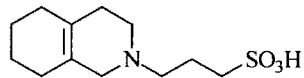 |
| 4-[2-(1,2,3,4,5,6,7,8-Octahydroisoquinolinyl)]-1-butanesulfonic acid | 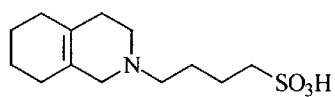 |

FIG. 13

Hexafluoroglutaric acid
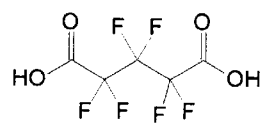
3,3-bis(trifluoromethyl)-2,2,4,4-tetrafluoro-1,5-pentanedioic acid
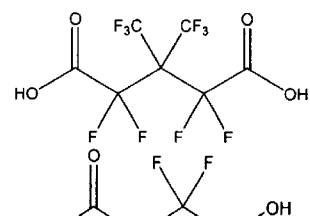
2,2,3,3-tetrafluoro-1,4-butanedioic acid
2,2,4,4,-tetrafluoro-1,5-pentanedioic acid
hexafluoro-1,3-propanedisulfinic acid
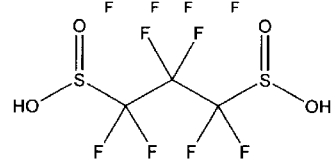
2,2-difluoro-1,3-propanedioic acid
3-hydroxyl-2,2,4,4,4-pentafluoro-3-phenylbutanoic acid
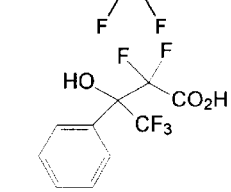
FIG. 14

METHODS AND COMPOUNDS FOR INHIBITING AMYLOID DEPOSITS

This application claims the benefit of priority under 35 U.S.C. 119(e) to copending U.S. Provisional Application No. 60/135,545, filed on May 24, 1999, and U.S. Provisional Application No. 60/143,123, filed on Jul. 9, 1999, the entire contents of which are incorporated herein by reference. This application is also related to U.S. Pat. No. 5,972,328, issued Oct. 26, 1999, the entire contents of which are incorporated herein by reference.

BACKGROUND OF THE INVENTION

Amyloidosis refers to a pathological condition characterized by the presence of amyloid. Amyloid is a generic term referring to a group of diverse but specific intra- and extracellular protein deposits which are associated with a number of different diseases. Though diverse in their occurrence, all amyloid deposits have common morphologic properties, including that they stain with specific dyes (e.g., Congo red), and have a characteristic birefringent appearance (sometimes characterized as "red-green") in polarized light after staining. They also share common ultrastructural features and common x-ray diffraction and infrared spectra.

Amyloidosis can be classified clinically as primary, secondary, familial and/or isolated. Isolated forms of amyloidosis are those that tend to involve a single organ system. Different amyloids are also characterized by the type of protein present in the deposit. For example, neurodegenerative diseases such as scrapie, bovine spongiform encephalitis, Creutzfeldt-Jakob disease and the like are characterized by the appearance and accumulation of a protease-resistant form of a prion protein (referred to as AScr or PrP-27) in the central nervous system. Similarly, Alzheimer's disease, another neurodegenerative disorder, is characterized by congophilic angiopathy, neuritic plaques and neurofibrillary tangles, all of which have the characteristics of amyloids. In this case, the plaque and blood vessel amyloid is formed by the beta protein. Other diseases, such as juvenile and adult-onset diabetes, complications of long-term hemodialysis and sequelae of long-standing inflammation or plasma cell dyscrasias are characterized by the accumulation of amyloids systemically. In each of these cases, a different amyloidogenic protein is involved in amyloid deposition.

Islet amyloid polypeptide (IAPP) is known to be capable of forming fibrils which are deposited in the pancreas of patients with Type II diabetes, forming deposits. Once these amyloid deposits have formed, there is no known therapy or treatment which significantly reduces or clears the deposits in situ.

SUMMARY OF THE INVENTION

This invention provides methods and compositions which are useful in the treatment of amyloidosis. In particular, methods and compositions are disclosed for inhibiting, preventing and treating amyloid deposition, e.g., in pancreatic islets wherein the amyloidotic deposits to be treated are, e.g., islet amyloid polypeptide (IAPP)-associated amyloid deposits having at least some β-sheet structure. The methods of the invention involve administering to a subject a therapeutic compound which inhibits, reduces or disrupts amyloid deposits, e.g., IAPP-associated amyloid deposits. Accordingly, the compositions and methods of the invention are useful for inhibiting amyloidosis in disorders in which such amyloid deposition occurs, such as diabetes.

In one embodiment, a method for inhibiting amyloid deposition, particularly IAPP-associated amyloid deposition, in a subject is provided, wherein an effective amount of an IAPP-inhibiting compound, or a pharmaceutically acceptable salt thereof, is administered to the subject such that said IAPP-associated amyloid deposition is inhibited. Such compounds include those of the following general formula

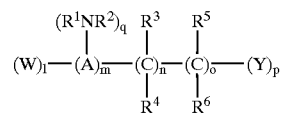

wherein C is carbon, N is nitrogen, l, m, o, p and q are independently 0 or 1; n is an integer from 0 to 3; W is hydrogen or an anionic group at physiological pH; Y is an anionic group at physiological pH; $R^1$ and $R^2$ are independently hydrogen, alkyl, an anionic group at physiological pH, or $R^1$ and $R^2$, taken together with the nitrogen to which they are attached, may form an unsubstituted or substituted heterocycle having from 3 to 7 atoms in the heterocyclic ring; $R^3$ is hydrogen, halogen, thiol or hydroxyl; $R^4$, $R^5$, and $R^6$ are independently hydrogen or halogen; and A is hydrogen or $C_1$ to $C_6$ alkyl; or a pharmaceutically acceptable ester, acid or salt thereof.

Preferred therapeutic compounds include 3-(3-hydroxy-1-propyl)amino-1-propanesulfonic acid; 2-amino-5-phosphovaleric acid; 4-phenyl-1-(3'-sulfopropyl)-1,2,3,6-tetrahydropyridine; cyclohexylsulfamic acid; O-phospho-L-serine; hexafluoroglutaric acid; 3-amino-2-hydroxy-1-propanesulfonic acid; 8-methoxy-5-quinolinesulfonic acid; and 3-dimethylamino-1-propanesulfonic acid, the compounds depicted in FIGS. 10–14, and pharmaceutically acceptable esters, acids or salts thereof.

In another embodiment a method for inhibiting amyloid deposition, particularly IAPP-associated amyloid deposition, in a subject is provided, wherein an effective amount of an IAPP-inhibiting compound, or a pharmaceutically acceptable ester, acid or salt thereof, is administered to the subject such that said IAPP-associated amyloid deposition is inhibited. Such compounds include those of the following general formula

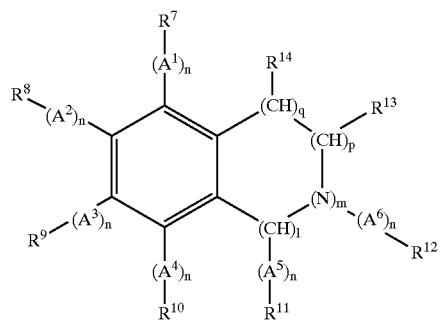

wherein $A^1$, $A^2$, $A^3$, $A^4$, $A^5$ and $A^6$ are independently alkyl, O, S, or —NH; m and n (for each individual A group) are independently 0 or 1; l, p and q are independently 0, 1, or 2; $R^7$, $R^8$, $R^9$, $R^{10}$, $R^{11}$, $R^{12}$, $R^{13}$, and $R^{14}$ are independently hydrogen, alkyl, alicyclyl, heterocyclyl or aryl, and adjacent R groups (e.g., $R^7$ and $R^8$) may form an unsubstituted or substituted cyclic or heterocyclic ring. In an embodiment, $R^{13}$ may be anionic.

Preferred therapeutic compounds include 1,2,3,4-tetrahydroisoquinoline, and the compounds depicted in FIGS. 1–9.

In another embodiment the invention relates to a method for reducing IAPP-associated amyloid deposits in a subject having IAPP-associated amyloid deposits, the method comprising administering to a subject an effective amount of an IAPP inhibiting compound, or a pharmaceutically acceptable ester, acid or salt thereof, such that IAPP-associated amyloid deposits are reduced.

The therapeutic compounds of the invention are administered to a subject by a route which is effective for inhibiting IAPP-associated amyloid deposition. Suitable routes of administration include oral, transdermal, subcutaneous, sublingual, buccal, intravenous and intraperitoneal injection. The therapeutic compounds can be administered with a pharmaceutically acceptable vehicle.

The invention further provides pharmaceutical compositions for treating amyloidosis. The pharmaceutical compositions include a therapeutic compound of the invention in an amount effective to inhibit IAPP-associated amyloid deposition, and a pharmaceutically acceptable vehicle.

BRIEF DESCRIPTION OF THE DRAWING

FIGS. 1–14 depict exemplary chemical structures of compounds described in the specification.

DETAILED DESCRIPTION OF THE INVENTION

The present invention will be more fully illustrated by reference to the definitions set forth below.

"Amyloid" includes IAPP-associated amyloid, including, but not limited to, β-sheet amyloid assembled substantially from IAPP subunits. "Inhibition" of amyloid deposition includes preventing or stopping of IAPP-associated amyloid formation, e.g., fibrillogenesis, inhibiting or slowing down of further IAPP-associated amyloid deposition in a subject with amyloidosis, e.g., already having amyloid deposits, and reducing or reversing IAPP-associated amyloid deposits in a subject with ongoing amyloidosis. Inhibition of amyloid deposition is determined relative to an untreated subject, or relative to the treated subject prior to treatment, or, e.g., determined by clinically measurable improvement in pancreatic function in a diabetic patient.

Pharmaceutically acceptable esters, acids or salts of the therapeutic compound, where applicable, are within the scope of the invention, e.g., alkali metal, alkaline earth metal, higher valency cation (e.g., aluminum salt), polycationic counter ion or ammonium salts. Where a compound is anionic, a preferred pharmaceutically acceptable salt is a sodium salt. Other salts are also contemplated, e.g., HCl, citric acid, tartaric acid salts, within their pharmaceutically acceptable ranges.

The therapeutic compound of the invention can be administered in a pharmaceutically acceptable vehicle. As used herein "pharmaceutically acceptable vehicle" includes any and all solvents, dispersion media, coatings, antibacterial and antifungal agents, isotonic and absorption delaying agents, and the like which are compatible with the activity of the compound and are physiologically acceptable to the subject. An example of a pharmaceutically acceptable vehicle is buffered normal saline (0.15 molar NaCl). Except insofar as any conventional media or agent is incompatible with the therapeutic compound, use thereof in the compositions suitable for pharmaceutical administration is contemplated. Supplementary active compounds can also be incorporated into the compositions.

An "anionic group," as used herein, refers to a group that is negatively charged at physiological pH. Preferred anionic groups include carboxylate, sulfate, sulfonate, sulfinate, sulfamate, tetrazolyl, phosphate, phosphonate, phosphinate, and phosphorothioate or functional equivalents thereof. "Functional equivalents" of anionic groups include bioisosteres, e.g., bioisosteres of a carboxylate group. Bioisosteres encompass both classical bioisosteric equivalents and non-classical bioisosteric equivalents. Classical and non-classical bioisosteres are known in the art (see, e.g., Silverman, R. B. *The Organic Chemistry of Drug Design and Drug Action*, Academic Press, Inc.: San Diego, Calif., 1992, pp.19–23). A particularly preferred anionic group is a carboxylate.

The term "alkyl" includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$–$C_{30}$ for straight chain, $C_3$–$C_{30}$ for branched chain), and more preferably has 20 or fewer carbon atoms in the backbone. Likewise, cycloalkyls may have from 4–10 carbon atoms in their ring structure, more preferably have 5, 6 or 7 carbons in the ring structure.

Moreover, the term alkyl includes both "unsubstituted alkyls" and "substituted alkyls", the latter of which refers to alkyl moieties having substituents replacing a hydrogen on one or more carbons of the hydrocarbon backbone. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfate, sulfonato, sulfamoyl, sulfonamido, nitro, trifluoromethyl, cyano, azido, heterocyclyl, or an aromatic or heteroaromatic moiety. It will be understood by those skilled in the art that the moieties substituted on the hydrocarbon chain can themselves be substituted, if appropriate. Cycloalkyls can be further substituted, e.g., with the substituents described above. An "aralkyl" moiety is an alkyl substituted with an aryl (e.g., phenylmethyl (benzyl)).

The term "aryl" herein includes 5- and 6-membered single-ring aromatic groups that may include from zero to four heteroatoms, for example, benzene, pyrrole, furan, thiophene, imidazole, oxazole, thiazole, triazole, tetrazole, pyrazole, pyridine, pyrazine, pyridazine and pyrimidine, and the like. Aryl groups also include polycyclic fused aromatic groups such as naphthyl, quinolyl, indolyl, and the like. Those aryl groups having heteroatoms in the ring structure may also be referred to as "aryl heterocycles", "heteroaryls" or "heteroaromatics". The aromatic ring can be substituted at one or more ring positions with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfate, sulfonato, sulfamoyl, sulfonamido, nitro, trifluoromethyl, cyano, azido, heterocyclyl, or an aromatic or heteroaromatic moiety. Aryl groups can also be fused or bridged with alicyclic or heterocyclic rings which are not aromatic so as to form a polycycle (e.g., tetralin).

The terms "alkenyl" and "alkynyl" include unsaturated aliphatic groups analogous in length and possible substitution to the alkyls described above, but that contain at least one double or triple bond respectively.

Unless the number of carbons is otherwise specified, "lower alkyl" means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls.

The terms "heterocyclyl" or "heterocyclic group" include 3- to 10-membered ring structures, more preferably 4- to 7-membered rings, which ring structures include one to four heteroatoms. Heterocyclyl groups include pyrrolidine, oxolane, thiolane, piperidine, piperazine, morpholine, lactones, lactams such as azetidinones and pyrrolidinones, sultams, sultones, and the like. The heterocyclic ring can be substituted at one or more positions with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfate, sulfonato, sulfamoyl, sulfonamido, nitro, trifluoromethyl, cyano, azido, heterocyclyl, or an aromatic or heteroaromatic moiety.

The terms "polycyclyl" or "polycyclic group" include two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfate, sulfonato, sulfamoyl, sulfonamido, nitro, trifluoromethyl, cyano, azido, heterocyclyl, or an aromatic or heteroaromatic moiety.

The term "heteroatom" includes an atom of any element other than carbon or hydrogen. Preferred heteroatoms are nitrogen, oxygen, sulfur and phosphorus.

The term "aryl aldehyde," as used herein, includes compounds represented by the formula Ar—C(O)H, in which Ar is an aryl moiety (as described above) and —C(O)H is a formyl or aldehydo group.

It will be noted that the structures of some of the compounds of this invention include asymmetric carbon atoms. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis. Furthermore, alkenes or alkynes can include either the E- or Z-geometry, where appropriate.

The present methods and compositions, in embodiments, inhibit, prevent and treat amyloid deposition in pancreatic islets wherein the amyloidotic deposits to be treated are islet amyloid polypeptide (IAPP)-associated amyloid deposits, e.g., having at least some β-sheet structure. The methods of the invention include administering to a subject a therapeutic compound which inhibits, reduces or disrupts IAPP-associated amyloid deposits. Accordingly, the compositions and methods of the invention are useful for inhibiting amyloidosis in disorders in which such amyloid deposition occurs, such as diabetes.

In one embodiment, a method for inhibiting IAPP-associated amyloid deposition in a subject is provided, wherein an effective amount of an IAPP-inhibiting compound, or a pharmaceutically acceptable ester, acid or salt thereof, is administered to the subject such that said IAPP-associated amyloid deposition is inhibited. Such compounds include those of the following general formula:

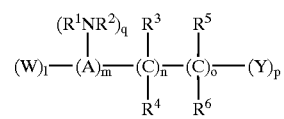

wherein C is carbon, N is nitrogen, l, m, o, p and q are independently 0 or 1; n is an integer from 0 to 3; W is hydrogen or an anionic group at physiological pH; Y is an anionic group at physiological pH; $R^1$ and $R^2$ are independently hydrogen, alkyl, an anionic group at physiological pH, or $R^1$ and $R^2$, taken together with the nitrogen to which they are attached, may form an unsubstituted or substituted heterocycle having from 3 to 7 atoms in the heterocyclic ring; $R^3$ is hydrogen, halogen, thiol or hydroxyl; $R^4$, $R^5$, and $R^6$ are independently hydrogen or halogen; and A is hydrogen or $C_1$ to $C_6$ alkyl; or a pharmaceutically acceptable ester, acid or salt thereof.

In an embodiment, W is preferably —COOH; Y is preferably —COOH, —SO$_3$H, —PO$_3$H$_2$, or —OP(O)(OH)$_2$; $R^1$ is preferably H, Me or hydroxypropyl; $R^2$ is preferably H, Me or —SO$_3$H; $R_3$ is preferably H, F, or OH; when $R^1$ and $R^2$, taken together with the nitrogen to which they are attached, form an unsubstituted or substituted heterocycle, preferred groups include

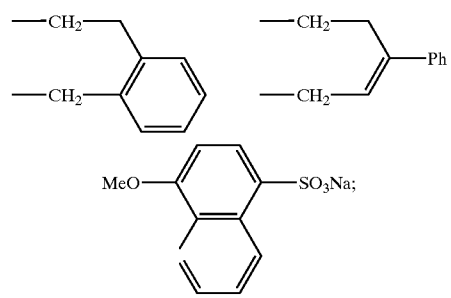

$R^4$, $R^5$ and $R^6$ are preferably H or F; A is preferably H, CH, CF$_2$ or alkyl which may be substituted or unsubstituted, straight, branched or cyclic, e.g., cyclohexyl.

Preferred therapeutic compounds include 3-(3-hydroxy-1-propyl)amino-1-propanesulfonic acid; 2-Amino-5- phosphovaleric acid; 4-phenyl-1-(3'-sulfopropyl)-1,2,3,6-tetrahydropyridine; cyclohexylsulfamic acid; O-phospho-L-serine; hexafluoroglutaric acid; 3-amino-2-hydroxy-1-propanesulfonic acid; 8-methoxy-5-quinolinesulfonic acid; and 3-dimethylamino-1-propanesulfonic acid, the compounds depicted in FIGS. 10–14, and pharmaceutically acceptable esters, acids or salts thereof.

In another embodiment, a method for inhibiting IAPP-associated amyloid deposition in a subject is provided, wherein an effective amount of an IAPP-inhibiting compound, or a pharmaceutically acceptable ester, acid or salt thereof, is administered to the subject such that said IAPP-associated amyloid deposition is inhibited. Such compounds include those of the following general formula:

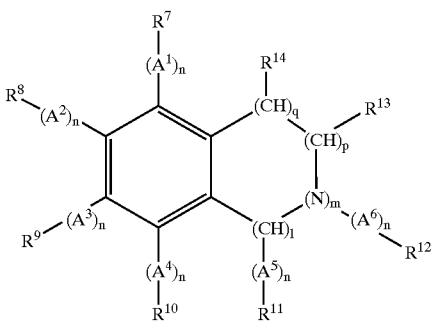

wherein $A^1$, $A^2$, $A^3$, $A^4$, $A^5$ and $A^6$ are independently alkyl, O, S, or —NH; m and n (for each individual A group) are independently 0 or 1; l, p and q are independently 0, 1, or 2; $R^7$, $R^8$, $R^9$, $R^{10}$, $R^{11}$, $R^{12}$, $R^{13}$, and $R^{14}$ are independently hydrogen, alkyl, alicyclyl, heterocyclyl or aryl, and adjacent R groups (e.g., $R^1$ and $R^2$) may form an unsubstituted or substituted cyclic or heterocyclic ring. In an embodiment, $R^{13}$ may be anionic.

Preferred therapeutic compounds include 1,2,3,4-tetrahydroisoquinoline, and the compounds depicted in FIGS. 1–9.

A further aspect of the invention includes pharmaceutical compositions for treating amyloidosis. The therapeutic compounds in the methods of the invention, as described hereinbefore, can be incorporated into a pharmaceutical composition in an amount effective to inhibit amyloidosis or reduce amyloid deposits, in a pharmaceutically acceptable vehicle.

In the methods of the invention, amyloid deposition in a subject is inhibited by administering a therapeutic compound of the invention to the subject. The term subject includes living organisms in which amyloidosis can occur. Examples of subjects include humans, apes, monkeys, cows, sheep, goats, dogs, cats, mice, rats, and transgenic species thereof. Administration of the compositions of the present invention to a subject to be treated can be carried out using known procedures, at dosages and for periods of time effective to inhibit amyloid deposition or reduce amyloid deposits in the subject. An effective amount of the therapeutic compound necessary to achieve a therapeutic effect may vary according to factors such as the amount of amyloid already deposited at the clinical site in the subject, the age, sex, and weight of the subject, and the ability of the therapeutic compound to inhibit amyloid deposition or reduce amyloid deposits in the subject. Dosage regimens can be adjusted to provide the optimum therapeutic response. For example, several divided doses may be administered daily or the dose may be proportionally reduced as indicated by the exigencies of the therapeutic situation.

The active compound may be administered by routes such as oral, sublingual, buccal, transdermal, subcutaneous, intravenous, and intraperitoneal administration. Depending on the route of administration, the active compound may be coated in a material to protect the compound from the action of acids, enzymes and other natural conditions which may inactivate the compound.

The compounds of the invention can be formulated to ensure proper distribution in vivo. For example, the therapeutic compounds of the invention can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs ("targeting moieties"), thus providing targeted drug delivery (see, e.g., V. V. Ranade (1989) *J. Clin. Pharmacol.* 29:685). Exemplary targeting moieties include folate or biotin (see, e.g., U.S. Pat. No. 5,416,016 to Low et al.); mannosides (Umezawa et al., (1988) *Biochem. Biophys. Res. Commun.* 153:1038); antibodies (P. G. Bloeman et al. (1995) *FEBS Lett.* 357:140; M. Owais et al. (1995) *Antimicrob. Agents Chemother.* 39:180); surfactant protein A receptor (Briscoe et al. (1995) *Am. J. Physiol.* 1233:134); gp120 (Schreier et al. (1994) *J. Biol. Chem.* 269:9090); see also K. Keinanen; M. L. Laukkanen (1994) *FEBS Lett.* 346:123; J. J. Killion; I. J. Fidler (1994) *Immunomethods* 4:273. In a preferred embodiment, the therapeutic compounds of the invention are formulated in liposomes; in a more preferred embodiment, the liposomes include a targeting moiety.

To administer the therapeutic compound by other than parenteral administration, it may be necessary to coat the compound with, or co-administer the compound with, a material to prevent its inactivation. For example, the therapeutic compound may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al., (1984) *J. Neuroimmunol.* 7:27).

The therapeutic compound may also be administered parenterally, sublingually, buccally, intraperitoneally, intraspinally, or intracerebrally. Dispersions can be prepared in, e.g., glycerol, liquid polyethylene glycols, and mixtures thereof, and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The vehicle can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic compound in the required amount in an appropriate solvent with one or a combination of ingredients enumerated above, as required, followed by filter sterilization. Generally, dispersions are prepared by incorporating the therapeutic compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yield a powder of the active ingredient (i.e., the therapeutic compound) plus any additional desired ingredient from a previously sterile-filtered solution thereof.

The therapeutic compound can be orally administered, for example, with an inert diluent or an assimilable edible carrier. The therapeutic compound and other ingredients may also be enclosed in a hard or soft shell gelatin capsule, compressed into tablets, or incorporated directly into the subject's diet. For oral therapeutic administration, the therapeutic compound may be incorporated with excipients and used in the form of ingestible tablets, sublingual/buccal tablets, troches, capsules, elixirs, suspensions, syrups, wafers, and the like. The percentage of the therapeutic compound in the compositions and preparations may, of course, be varied. The amount of the therapeutic compound in such therapeutically useful compositions is such that a suitable dosage will be obtained.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical vehicle. The specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of amyloid deposition in subjects.

Active compounds are administered at a therapeutically effective dosage sufficient to inhibit amyloid deposition in a subject. A "therapeutically effective dosage" preferably inhibits amyloid deposition and/or reduces amyloid deposits by at least about 20%, more preferably by at least about 40%, even more preferably by at least about 60%, and still more preferably by at least about 80% relative to untreated subjects or to the same subject prior to treatment.

The ability of a compound to inhibit amyloid deposition or reduce amyloid deposits can be evaluated in an animal model system that may be predictive of efficacy in inhibiting amyloid deposition or reducing amyloid deposits in human diseases. The ability of a compound to inhibit amyloid deposition can also be evaluated by examining the ability of the compound to inhibit amyloid deposition in vitro or ex vivo, e.g., using an ELISA assay. The effect of a compound on the secondary structure of the amyloid can further be determined by thioflavine T (ThT) assay, circular dichroism (CD) or infrared (IR) spectroscopy.

CD and IR spectroscopy are particularly useful techniques because the information obtained is a direct measure of the ability of a test compound to prevent or reverse amyloidosis, by determining the structural effect of a compound on amyloid protein folding and/or fibril formation. This contrasts with previously known methods which measure cellular trafficking of amyloid protein precursors or interactions between amyloid and extracellular matrix proteins, providing only indirect evidence of potential amyloid-inhibiting activity. It should further be noted that CD and IR spectroscopy can also detect compounds which cause an increase in, e.g., β-sheet folding of amyloid protein, and thereby stabilize the formation of amyloid fibrils.

The deposition of amyloid is a multi-stage process. Accordingly, an agent useful for treating amyloidosis has many potential modes of action. An agent which inhibits amyloid deposition could act in one or more of the following ways, which are shown by way of illustration and not limitation:

1. Inhibition or delay of protein folding in solution;
2. Inhibition or delay of aggregation/elongation of oligomerized amyloid peptides into fibrils and/or deposits; and
3. Disruption/dissolution/modification of amyloid fibrils and/or deposits;

Categories 1 and 2 correspond to prevention of the formation of amyloid deposits (slowing down or halting amyloid deposition), and category 3 corresponds to removal or modification of deposits already formed (removal or reduction of existing amyloid deposits).

The invention is further illustrated by the following examples which should not be construed as further limiting the subject invention.

EXAMPLE 1

Determination of the rate of amyloid fibril formation by Thioflavine T spectroscopy Thioflavine T (ThT) binds to amyloid proteins in β-sheet formation, exhibiting a yellow fluorescence from tissue sections and fibrils in vitro. Detection of ThT fluorescence can be used as a sensitive assay for amyloid fibril formation under different conditions. This assay has been used in experiments to determine the effects of compounds of the invention on amyloid fibril formation.

Method

Synthetic human IAPP (Bachem) was dissolved in 40% trifluoroethanol and freeze-dried into conveniently-sized aliquots. IAPP was prepared immediately before the measurements by dissolving in 40% 1,1,1,3,3,3-hexafluoro-2-propanol (HFIP) in water to maintain the peptide in alpha helical conformation and soluble. A stock solution of ThT (2.5 mM) was prepared, 7.9 mg in 10 mL Tris-HCl pH 7.0 and filtered (0.22 $\mu$m). Solutions were kept in the dark until use. Fluorescence was examined at 440 nm excitation (slit 5 nm), and emission at 482 nm (slit 10 nm) with stirring. 25 ml of ThT stock (final concentration 62.5 $\mu$M) was added to peptide sample and made up to 1 mL in the cuvette. The sample was stirred for 5 min. before taking a reading. Measurements were made at an initial time point (5 min. from sample preparation), at intervals over the next 4–6 h and after overnight incubation at room temperature.

Certain compounds (or their salts, as noted) as disclosed herein, i.e., 3-(3-hydroxy-1-propyl)amino-1-propanesulfonic acid; 2-amino-5-phosphovaleric acid; 4-phenyl-1-(3'-sulfopropyl)-1,2,3,6-tetrahydropyridine; cyclohexylsulfamic acid; O-phospho-L-serine; hexafluoroglutaric acid; 8-methoxy-5-quinolinesulfonic acid; 3-amino-2-hydroxy-1-propanesulfonic acid; and 3-dimethylamino-1-propanesulfonic acid, and 1,2,3,4-tetrahydroisoquinoline, were found, using this assay, to inhibit or prevent IAPP-associated fibril assembly.

EXAMPLE 2

Circular dichroism analysis was conducted to confirm the activity of certain therapeutic compounds in preventing or inhibiting IAPP-associated fibril formation in accordance with the present disclosure by determining the presence or absence of β-sheet conformation. The results are presented in Table 1.

The assay is conducted as follows:
INSTRUMENT AND PARAMETERS
Instrument: JASCO J-715 Spectropolarimeter
Cell/cuvette: Hellma quartz (QS) with 1.0 mm pathlength
Room temperature
Wavelength interval: 250 nm–190 nm
Resolution: 0.1 nm
Band width: 1.0 nm
Response time: 1 sec
Scanning speed: 20 nm/min
Number of spectra run: 5

The assay, a co-incubation procedure, examines the ability of a compound or substance to inhibit the assembly of amyloid fibrils, e.g., to test for the presence of the amyloidotic β-sheet conformation in the presence of soluble IAPP. Samples are run in the presence and absence (i.e., water alone) of buffering agent, which is done to determine if competitive effects are seen with the ionic buffer (usually phosphate).

A. Assay in Water Only

Add components used at a molar ratio of 1:10 [peptide:compound]; add 10 μL of 10 mg/mL IAPP stock solution (final 100 μg peptide) to the aqueous solution containing compound to a final volume of 400 μl. The pH of the final assay solution is measured to ensure there is no fluctuation and the spectrum is accumulated using the parameters as shown above.

B. Assay in Phosphate Buffer

Add desired amount of compound to achieve a 1:10 molar ratio in 10 mM phosphate buffer, pH 7. Add 10 μL of 10 mg/mL IAPP stock solution (final peptide 100 μg) to the phosphate buffered solution containing the compound and bring to a final volume of 400 μL. The pH of the final assay solution is measured to ensure there is no fluctuation and the spectrum is accumulated using the parameters as shown above.

In both assays, a control sample is run with each test group. This control contains peptide only in water or buffer at a similar final volume of 400 μl. Spectra for the control are collected initially (first run) and at the end of the test (final run) to ensure that the peptide has not undergone extensive aggregation during the course of the assay. Spectra for the controls are used to compare with the measurements obtained with the treated samples.

CO-INCUBATION

Make fresh 1 mg/mL stock solution of IAPP in 10 mM phosphate buffer, pH 7. Add desired amount of compound to achieve a 1:10 molar ratio in 10 mM phosphate buffer, pH 7. Incubate for 3 days at room temperature. Make up to final volume of 400 μL with 10 mM phosphate buffer, pH 7. The pH of the final assay solution is measured to ensure there is no fluctuation and the spectrum is accumulated using the parameters as shown above.

A similar control is run for comparative purposes.

DATA ANALYSIS

Plots of the spectra (control and treated) are individually assembled and the changes in ellipticity at 218 nm are examined. This minimum is directly correlated with the amount of β-sheet present in the sample. Changes in either a positive or negative direction are noted and a relative value ("active" or "not active") assigned to the compound as a measure of activity.

TABLE 1

| Compound | Activity |
| --- | --- |
| 3-(3-hydroxy-1-propyl)amino-1-propanesulfonic acid | Active |
| DL-2-amino-5-phosphovaleric acid | Active |
| 1,2,3,4-tetrahydroisoquinoline, HCl | Active |
| cyclohexylsulfamic acid, sodium salt | Active |
| O-phospho-L-serine | Active |
| hexafluoroglutaric acid | Active |
| 8-methoxyquinoline-5-sulfonic acid, sodium salt | Active |
| 4-phenyl-1-(3'-sulfopropyl)-1,2,3,6-tetrahydropyridine, sodium salt | Active |
| 3-amino-2-hydroxy-1-propanesulfonic acid | Active |
| 3-dimethylamino-1-propanesulfonic acid | Active |

EXAMPLE 3

The synthesis of a compound of the invention, 4-phenyl-1-(3'-sulfopropyl)-1,2,3,6-tetrahydropyridine, in the sodium salt form, is described below.

To a solution of 4-phenylpyridine (15.5 g, 0.1 mol) in acetone (100 mL) was added 1,3-propane sultone (12.2 g, 0.1 mol) at room temperature. The mixture was then heated at reflux temperature overnight. The resultant suspension was cooled to room temperature. The solid was collected by filtration and washed with acetone. To a solution of the solid (31 g) in methanol (500 mL) was added sodium borohydride (10 g, 260 mmol) portionwise, and the mixture was stirred at room temperature for 2 h. Distilled water (50 mL) was added to destroy the excess of sodium borohydride. The mixture was diluted with methanol (200 ml), and neutralized with Amberlite IR-120 ion-exchange resin ($H^+$ form, 300 g). A white precipitate was formed. The precipitate and the resin were removed by filtration and treated with distilled water (400 mL) at ~100 °C. The mixture was filtered and the residual resin was washed with hot distilled water (2×200 mL). The filtrates and washings were combined and concentrated to dryness. The residue was co-evaporated with methanol (3×200 mL), and then recrystallized from ethanol-water {8:2 (v/v)} to afford 4-phenyl-1-(3'-sulfopropyl)-1,2,3,6-tetrahydropyridine as white crystals (26 g, 93%). The $^1H$ and $^{13}C$ NMR spectra were in agreement with the structure.

To a solution of 4-phenyl-1-(3'-sulfopropyl)-1,2,3,6-tetrahydropyridine (5.6 g, 20 mmol) obtained above in ethanol (180 mL) was added sodium hydroxide (1.2 g, 30 mmol). The suspension was heated at reflux temperature for 30 min. The mixture was then cooled to room temperature. The first crop of product (3.9 g, 64%) was collected by filtration. The filtrate was concentrated to dryness, and the residue was recrystallized from ethanol to afford the second crop of product (2.0 g, 32%). $^1H$ NMR (400 MHz, $D_2O$): δ 1.85 (quintet, 2H, J 8.7, 7.7 Hz, 2H-2'), 2.39–2.45 (m, 4H, 2H-3' and 2H-3), 2.59 (t, 2H, J 5.6 Hz, 2H-2), 2.80 (t, 2H, J 7.7 Hz, 2H-1'), 3.00 (br s, 2H, 2H-6), 6.00 (br s, 1H, H-5), 7.18–7.36 (m, 5H, Ar). $^{13}C$ NMR (100.6 MHz, $D_2O$): δ 23.90 (C-2'), 29.01 (C-3), 51.69, 51.76 (C-2, C-3'), 54.45 (C-6), 58.12 (C-1'), 123.75 (C-5), 127.31, 130.01, 131.24 (Ar), 136.89 (C-4), 142.47 (Ar).

EQUIVALENTS

Those skilled in the art will recognize, or be able to ascertain using no more than routine experimentation, numerous equivalents to the specific procedures described herein. Such equivalents are considered to be within the scope of this invention and are covered by the following claims. The contents of all references, issued patents, and published patent applications cited throughout this application are hereby incorporated by reference.

What is claimed is:

1. A method for inhibiting IAPP-associated amyloid deposits in a subject, comprising administering to said subject an effective amount of an IAPP-inhibiting compound, or a pharmaceutically acceptable ester, acid or salt thereof, such that said IAPP-associated amyloid deposits are inhibited, wherein said IAPP-inhibiting compound is of the formula

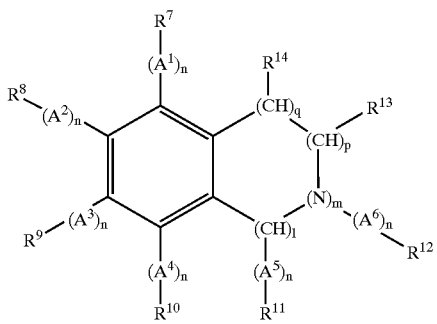

wherein $A^1$, $A^2$, $A^3$, $A^4$, $A^5$ and $A^6$ are independently alkyl, O, S, or —NH; n (for each individual A group) is 0 or 1; m is 1; l, p and q are independently 0, 1, or 2; $R^7$, $R^8$, $R^9$, $R^{10}$, $R^{11}$, $R^{12}$, $R^{13}$, and $R^{14}$ are independently hydrogen, an anionic group at physiological pH, alkyl, alicyclyl, heterocyclyl or aryl, and adjacent R groups may form an unsubstituted or substituted cyclic or heterocyclic ring.

2. A method for reducing IAPP-associated amyloid deposits in a subject having IAPP-associated amyloid deposits, the method comprising administering to said subject an effective amount of an IAPP inhibiting compound, or a pharmaceutically acceptable ester, acid or salt thereof, such that said IAPP-associated amyloid deposits are inhibited, wherein said IAPP-inhibiting compound is of the formula

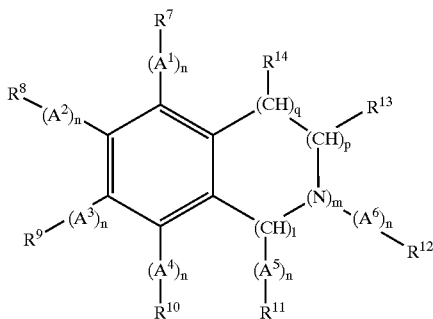

wherein $A^1$, $A^2$, $A^3$, $A^4$, $A^5$ and $A^6$ are independently alkyl, O, S, or —NH; n (for each individual A group) is 0 or 1; m is 1; l, p and q are independently 0, 1, or 2; $R^7$, $R^8$, $R^9$, $R^{10}$, $R^{11}$, $R^{12}$, $R^{13}$, and $R^{14}$ are independently hydrogen, an anionic group at physiological pH, alkyl, alicyclyl, heterocyclyl or aryl, and adjacent R groups may form an unsubstituted or substituted cyclic or heterocyclic ring.

3. The method of claim 1, wherein said subject has IAPP-associated amyloid deposits in pancreatic islets.

4. The method of claim 2, wherein said subject has IAPP associated amyloid deposits in pancreatic islets.

5. The method of claim 2, wherein said compound is selected from the group consisting of the compounds 3-[2-(1,2,3,4-tetrahydroisoquinolinyl)]-1-propanesulfonic acid, and pharmaceutically acceptable esters, acids, and salts thereof.

6. The method of claim 2, wherein said compound is selected from the group consisting of the comnpounds 3-[2-(6,7-dimethoxy-1,2,3,4-tetrahydroisoquinolinyl)]-1-propanesulfonic acid, and pharmaceutically acceptable esters, acids, and salts thereof.

7. The method of claim 2, wherein said compound is selected from the group consisting of the compounds 3-[2-(6-methoxy-1,2,3,4-tetrahydro-isoquinolinyl)]-1-propanesulfonic acid, and pharmaceutically acceptable esters, acids, and salts thereof.

8. The method of claim 2, wherein said compound is selected from the group consisting of the compounds 2-(2-sulfobenzoyl)-1,2,3,4-tetrahydroisoquinoline, and pharmaceutically acceptable esters, acids, and salts thereof.

9. The method of claim 2, wherein said compound is selected from the group consisting of the compounds 2-(2-sulfobenzyl)-1,2,3,4-tetrahydroisoquinoline, and pharmaceutically acceptable esters, acids, and salts thereof.

10. The method of claim 2, wherein said compound is selected from the group consisting of the compounds 1,2,3,4-tetrahydroisoquinoline, and pharmaceutically acceptable esters, acids, and salts thereof.

11. The method of claim 2, wherein said compound is selected from the group consisting of the compounds 3-[2-(3-carboxy-1,2,3,4-tetrahydroisoquinolinyl)]-1-propanesulfonic acid, and pharmaceutically acceptable esters, acids, and salts thereof.

12. The method of claim 2, wherein said compound is selected from the group consisting of the compounds N-methyl-N-phenyl-3-[2-(1,2,3,4-tetrahydroisoquinolinyl)]-1-propanesulfonamide, and pharmaceutically acceptable esters, acids, and salts thereof.

13. The method of claim 2, wherein said compound is selected from the group consisting of the compounds 4-[2-(1,2,3,4-tetrahydroisoquinolinyl)]-1-butanesulfonic acid, and pharmaceutically acceptable esters, acids, and salts thereof.

14. The method of claim 2, wherein said compound is selected from the group consisting of the compounds 4-[2-(6,7-dimethoxy-1,2,3,4-tetrahydroisoquinolinyl)]-1-butanesulfonic acid, and pharmaceutically acceptable esters, acids, and salts thereof.

15. The method of claim 2, wherein said compound is selected from the group consisting of the compounds 4-[2-(6-methoxy-1,2,3,4-tetrahydroisoquinolinyl)]-1-butanesulfonic acid, and pharmaceutically acceptable esters, acids, and salts thereof.

16. The method of claim 2, wherein said compound is selected from the group consisting of the compounds 3-[2-(1,2,3,4-tetrahydroisoquinolinyl)]-1-propylthiophosphonic acid, and pharmaceutically acceptable esters, acids, and salts thereof.

17. The method of claim 2, wherein said compound is selected from the group consisting of the compounds 3-[2-(6methoxy-1,2,3,4-tetrahydroisoquinolinyl)]-1-propanesulfonic acid, and pharmaceutically acceptable esters, acids, and salts thereof.

18. The method of claim 2, wherein said compound is selected from the group consisting of the compounds 3-[2-(8-methoxy-1,2,3,4-tetrahydroisoquinolinyl)]-1-propanesulfonic acid, and pharmaceutically acceptable esters, acids, and salts thereof.

19. The method of claim 2, wherein said compound is selected from the group consisting of the compounds 1,2,3, 4-tetrahydro-8-isoquinolinesulfonic acid, and pharmaceutically acceptable esters, acids, and salts thereof.

20. The method of claim 2, wherein said compound is selected from the group consisting of the compounds 3-[2-(6-dimethylamino-1,2,3,4-tetrahydroisoquinolinyl)]-1-propanesulfonic acid, and pharmaceutically acceptable esters, acids, and salts thereof.

21. The method of claim 2, wherein said compound is selected from the group consisting of the compounds 3-[2-(6-chloro-1,2,3,4-tetrahydroisoquinolinyl)]-1-propanesulfonic acid, and pharmaceutically acceptable esters, acids, and salts thereof.

22. The method of claim 2, wherein said compound is selected from the group consisting of the compounds 4-[2-(1,2,3,4-tetrahydroisoquinolinyl)]-1-butanesulfonic acid, and pharmaceutically acceptable esters, acids, and salts thereof.

23. The method of claim 2, wherein said compound is selected from the group consisting of the compounds 1,2,3,4-tetrahydro-5-isoquinolinesulfonic acid, and pharmaceutically acceptable esters, acids, and salts thereof.

24. The method of claim 2, wherein said compound is selected from the group consisting of the compounds 1-sulfopropyl-2-[2-(1,2,3,4-tetrahydroisoquinolinyl) methyl]-4,5-dihydroimidazole, and pharmaceutically acceptable esters, acids, and salts thereof.

25. The method of claim 2, wherein said compound is selected from the group consisting of the compounds 3-[7-methoxy-2-(1,2,3,4-tetrahydroisoquinolinyl)] propylphosphonic acid, and pharmaceutically acceptable esters, acids, and salts thereof.

26. The method of claim 2, wherein said compound is selected from the group consisting of the compounds 3-[6-methoxy-2-(1,2,3,4-tetrahydroisoquinolinyl)] propylphosphonic acid, and pharmaceutically acceptable esters, acids, and salts thereof.

27. The method of claim 2, wherein said compound is selected from the group consisting of the compounds 3-[8-methoxy-2-(1,2,3,4-tetrahydroisoquinolinyl)] propylphosphonic acid, and pharmaceutically acceptable esters, acids, and salts thereof.

28. The method of claim 2, wherein said compound is selected from the group consisting of the compounds 3-[2-(3-methoxycarbonyl-1,2,3,4-tetrahydroisoquinolinyl)] propylphosphonic acid, and pharmaceutically acceptable esters, acids, and salts thereof.

29. The method of claim 2, wherein said compound is selected from the group consisting of the compounds 3-[6-methoxy-2-(1,2,3,4-tetrahydroisoquinolinyl)] propylphosphonic acid, and pharmaceutically acceptable esters, acids, and salts thereof.

30. The method of claim 2, wherein said compound is selected from the group consisting of the compounds 3-[7-methoxy-2-(1,2,3,4tetrahydroisoquinolinyl)] propylphosphonic acid, and pharmaceutically acceptable esters, acids, and salts thereof.

31. The method of claim 2, wherein said compound is selected from the group consisting of the compounds N-phosphonoacetyl-6-methoxy-1,2,3,4-tetrahydroisoquinoline, and pharmaceutically acceptable esters, acids, and salts thereof.

32. The method of claim 2, wherein said compound is selected from the group consisting of the compounds 6-methoxy-1,2,3,4-tetrahydroisoquinoline, and pharmaceutically acceptable esters, acids, and salts thereof.

33. The method of claim 2, wherein said compound is selected from the group consisting of the compounds N-sulfoacetyl-1,2,3,4-tetrahydroisoquinoline, and pharmaceutically acceptable esters, acids, and salts thereof.

34. The method of claim 2, wherein said compound is selected from the group consisting of the compounds N-ethyl-1,2,3,4-tetrahydroisoquinoline, and pharmaceutically acceptable esters, acids, and salts thereof.

35. The method of claim 2, wherein said compound is selected from the group consisting of the compounds N-propyl-1,2,3,4-tetrahydroisoquinoline, and pharmaceutically acceptable esters, acids, and salts thereof.

36. The method of claim 2, wherein said compound is selected from the group consisting of the compounds N-propyl-6-methoxy-1,2,3,4-tetrahydroisoquinoline, and pharmaceutically acceptable esters, acids, and salts thereof.

37. The method of claim 2, wherein said compound is selected from the group consisting of the compounds 5-[(1,2,3,4-tetrahydroisoquinol-2-yl)methyl]isoxazol-3-ol, and pharmaceutically acceptable esters, acids, and salts thereof.

38. The method of claim 2, wherein said compound is selected from the group consisting of the compounds 5-[(6-methoxy-1,2,3,4-tetrahydroisoquinol-2-yl)methyl]isoxazol-3-ol, and pharmaceutically acceptable esters, acids, and salts thereof.

39. The method of claim 2, wherein said compound is selected from the group consisting of the compounds (±)-laudanosoline, and pharmaceutically acceptable esters, acids, and salts thereof.

40. The method of claim 2, wherein said compound is selected from the group consisting of the compounds (−)-1-[5-chloro-2-(methylamino)phenyl]-1,2,3,4-tetrahydroisoquinoline (−)-tartrate, and pharmaceutically acceptable esters, acids, and salts thereof.

41. The method of claim 2, wherein said compound is selected from the group consisting of the compounds (S)-(−)-1,2,3,4-tetrahydro-3-isoquiolinecarboxylic acid, and pharmaceutically acceptable esters, acids, and salts thereof.

42. The method of claim 2, wherein said compound is selected from the group consisting of the compounds tetrahydropapaveroline hydrobromide (norlaudanosoline hydrobromide), and pharmaceutically acceptable esters, acids, and salts thereof.

43. The method of claim 2, wherein said compound is selected from the group consisting of the compounds 3-phenyl-5-[2-(1,2,3,4-tetrahydroisoquinolyl)methyl] isoxazole, and pharmaceutically acceptable esters, acids, and salts thereof.

44. The method of claim 2, wherein said compound is selected from the group consisting of the compounds 3-methyl-5-[2-(1,2,3,4-tetrahydroisoquinolyl)methyl] isoxazole, and pharmaceutically acceptable esters, acids, and salts thereof.

45. The method of claim 2, wherein said compound is selected from the group consisting of the compomnds 5-[2-(1,2,3,4-tetrahydroisoquinolyl)methyl]isoxazole-3-carboxylic acid, and pharmaceutically acceptable esters, acids, and salts thereof.

46. The method of claim 2, wherein said compound is selected from the group consisting of the compounds 5-phenyl-3-[2-(1,2,3,4-tetrahydroisoquinolinyl)methyl] isoxazole, and pharmaceutically acceptable esters, acids, and salts thereof.

47. The method of claim 2, wherein said compound is selected from the group consisting of the compounds 3-[2-(1,2,3,4-tetrahydroisoquinolyl)methyl]isoxazole-5-carboxylic acid, and pharmaceutically acceptable esters, acids, and salts thereof.

48. The method of claim 2, wherein said compound is selected from the group consisting of the compounds (2S)-

2-amino-2-[3-(2-1,2,3,4-tetrahydroisoquinolylmethyl) isoxazol-5-yl]acetic acid, and pharmaceutically acceptable esters, acids, and salts thereof.

49. The method of claim 2, wherein said compound is selected from the group consisting of the compounds 3-[2-(1,2,3,4-tetrahydroisoquinolyl)-methyl]isoxazole-5-L-alanine, and pharmaceutically acceptable esters, acids, and salts thereof.

50. The method of claim 2, wherein said compound is selected from the group consisting of the compounds 4-[2-(1,2,3,4-tetrahydroisoquinolyl)methyl]-L-phenylalanine, and pharmaceutically acceptable esters, acids, and salts thereof.

51. The method of claim 2, wherein said compound is selected from the group consisting of the compounds 5-[2-(1,2,3,4-tetrahydroisoquinolyl)methyl)-1H-1,2,3,4-tetrazole, and pharmaceutically acceptable esters, acids, and salts thereof.

52. The method of claim 2, wherein said compound is selected from the group consisting of the compounds 5-(1,2,3,4-tetrahydroisoquinol-6-yl)-1H-1,2,3,4-tetrazole, and pharmaceutically acceptable esters, acids, and salts thereof.

53. The method of claim 2, wherein said compound is selected from the group consisting of the compounds 5-[6-(1,2,3,4-tetrahydroisoquinolyl)methyl)-1H-1,2,3,4-tetrazole, and pharmaceutically acceptable esters, acids, and salts thereof.

54. The method of claim 2, wherein said compound is selected from the group consisting of the compounds 5-{2-[6-(1,2,3,4-tetrahydroisoquinolyl)]ethyl}-1H-1,2,3,4-tetrazole, and pharmaceutically acceptable esters, acids, and salts thereof.

55. The method of claim 2, wherein said compound is selected from the group consisting of the compounds 5-(1,2,3,4-tetrahydroisoquinol-7yl)-1H-1,2,3,4-tetrazole, and pharmaceutically acceptable esters, acids, and salts thereof.

56. The method of claim 2, wherein said compound is selected from the group consisting of the compounds 5-[7-(1,2,3,4-tetrahydroisoquinolyl)methyl)-1H-1,2,3,4-tetrazole, and pharmaceutically acceptable esters, acids, and salts thereof.

57. The method of claim 2, wherein said compound is selected from the group consisting of the compounds 5-{2-[7-(1,2,3,4-tetrahydroisoquinolyl)]ethyl}-1H-1,2,3,4-tetrazole, and pharmaceutically acceptable esters, acids, and salts thereof.

58. The method of claim 2, wherein said compound is selected from the group consisting of the compowuds 6-methoxy-1,2,3,4-tetrahydroisoquinoline, and pharmaceutically acceptable esters, acids, and salts thereof.

59. The method of claim 2, wherein said compound is selected from the group consisting of the compounds 7-methoxy-1,2,3,4-tetrahydroisoquinoline, and pharmaceutically acceptable esters, acids, and salts thereof.

60. The method of claim 2, wherein said compound is selected from the group consisting of the compounds 6,7-dimethoxy-1,2,3,4-tetrahydroisoquinoline, and pharmaceutically acceptable esters, acids, and salts thereof.

61. The method of claim 2, wherein said compound is selected from the group consisting of the compounds 1,2,3,4-tetrahydroisoquinoline-6-carbonitrile, and pharmaceutically acceptable esters, acids, and salts thereof.

62. The method of claim 2, wherein said compound is selected from the group consisting of the compounds 1,2,3,4-tetrahydroisoquinoline-7-carbonitrile, and pharmaceutically acceptable esters, acids, and salts thereof.

63. The method of claim 2, wherein said compound is selected from the group consisting of the compounds 6-amino-1,2,3,4-tetrahydroisoquinoline, and pharmaceutically acceptable esters, acids, and salts thereof.

64. The method of claim 2, wherein said compound is selected from the group consisting of the compounds 7-amino-1,2.3,4-tetrahydroisoquinoline, and pharmaceutically acceptable esters, acids, and salts thereof.

65. The method of claim 2, wherein said compound is selected from the group consisting of the compounds 7-(3,4,5-trimethoxybenzoyl)amino-1,2,3,4-tetrahydroisoquinoline, and pharmaceutically acceptable esters, acids, and salts thereof.

66. The method of claim 2, wherein said compound is selected from the group consisting of the compounds 7-β-D-glucopyranosyl-6-methoxy-1,2,3,4-tetrahydroisoquinoline, and pharmaceutically acceptable esters, acids, and salts thereof.

67. The method of claim 2, wherein said compound is selected from the group consisting of the compounds 6-β-D-glucopyranosyl-7-methoxy-1,2,3,4-tetrahydroisoquinoline, and pharmaceutically acceptable esters, acids, and salts thereof.

68. The method of claim 2, wherein said compound is selected from the group consisting of the compounds (1,2,3,4-tetrahydroisoquinol-1-yl)phosphonic acid, and pharmaceutically acceptable esters, acids, and salts thereof.

69. The method of claim 2, wherein said compound is selected from the group consisting of the compounds 5,6,7,8-tetrahydro-2H-1,3-dioxoleno[4,5-g]isoquinoline, and pharmaceutically acceptable esters, acids, and salts thereof.

70. The method of claim 2, wherein said compound is selected from the group consisting of the compounds 1,2,3,4-tetrahydrobenzo[g]isoquinoline, and pharmaceutically acceptable esters, acids, and salts thereof.

71. The method of claim 2, wherein said compound is selected from the group consisting of the compounds (1,2 3,4-tetrahydroisoquinol-7-ylsulfonyl)aminobenzene, and pharmaceutically acceptable esters, acids, and salts thereof.

72. The method of claim 2, wherein said compound is selected from the group consisting of the compounds 1-[(1,2,3,4-tetrahydroisoquinol-7-ylsulfonyl)amino]-3,4-dichlorobenzene, and pharmaceutically acceptable esters, acids, and salts thereof.

73. The method of claim 2, wherein said compound is selected from the group consisting of the compounds 7-(2,2,2-trifluoroacetyl)-1,2,3,4-tetrahydroisoquinoline, and pharmaceutically acceptable esters, acids, and salts thereof.

74. The method of claim 2, wherein said compound is selected from the group consisting of the compounds 7-benzyl-1,2,3,4-tetrahydroisoquinoline, and pharmaceutically acceptable esters, acids, and salts thereof.

75. The method of claim 2, wherein said compound is selected from the group consisting of the compounds 7-benzoyl-1,2,3,4-tetrahydroisoquinoline, and pharmaceutically acceptable esters, acids, and salts thereof.

76. The method of claim 2, wherein said compound is selected from the group consisting of the compounds 7-acetyl-1,2,3,4-tetrahydroisoquinoline, and pharmaceutically acceptable esters, acids, and salts thereof.

77. The method of claim 2, wherein said compound is selected from the group consisting of the compounds 1,2,3,4-tetrahydroisoquoline-7-carboxylic acid, and pharmaceutically acceptable esters, acids, and salts thereof.

78. The method of claim 2, wherein said compound is selected from the group consisting of the compounds 1,2,3,4-tetrahydroisoquinoline-7-carboxamide, and pharmaceutically acceptable esters, acids, and salts thereof.

79. The method of claim 2, wherein said compound is selected from the group consisting of the compounds 7-aminomethyl-1,2,3,4-tetrahydroisoquinoline; and pharmaceutically acceptable esters, acids, and salts thereof.

80. The method of claim 2, wherein said compound is selected from the group consisting of the compounds 7-hydroxymethyl-1,2,3,4-tetrahydroisoquinoline, and pharmaceutically acceptable esters, acids, and salts thereof.

81. The method of claim 2, wherein said compound is selected from the group consisting of the compounds 7-methyl-1,2,3,4-tetrahydroisoquinoline, and pharmaceutically acceptable esters, acids, and salts thereof.

82. The method of claim 2, wherein said compound is selected from the group consisting of the compounds 7-hydroxy-1,2,3,4-tetrahydroisoquinoline, and pharmaceutically acceptable esters, acids, and salts thereof.

83. The method of claim 2, wherein said compound is selected from the group consisting of the compounds 7-(methanesulfonyl)amino-1,2,3,4-tetrahydroisoquinoline, and pharmaceutically acceptable esters, acids, and salts thereof.

84. The method of claim 2, wherein said compound is selected from the group consisting of the compounds 7-(methanesulfonyl)aminomethyl-1,2,3,4-tetrahydroisoquinoline, and pharmaceutically acceptable esters, acids, and salts thereof.

85. The method of claim 2, wherein said compound is selected from the group consisting of the compounds 7-nitro-1,2,3,4-tetrahydroisoquinoline, and pharmaceutically acceptable esters, acids, and sats thereof.

86. The method of claim 2, wherein said compound is selected from the group consisting of the compounds 1,2,3,4-tetrahydroisoquinoline-7-sulfonamide, and pharmaceutically acceptable esters, acids, and salts thereof.

87. The method of claim 2, wherein said compound is selected from the group consisting of the compounds 7-trifluoromethyl-1,2,3,4-tetrahydroisoquinoline, and pharmaceutically acceptable esters, acids, and salts thereof.

88. The method of claim 2, wherein said compound is selected from the group consisting of the compounds 7-methylthio-1,2,3,4-tetrahydroisoquinoline, an pharmaceutically acceptable esters, acids, and salts thereof.

89. The method of claim 1, wherein said IAPP-inhibiting compound is selected from the group consisting of the compounds 3-[2-(1,2,3,4-tetrahydroisoquinolinyl)]-1-propanesulfonic acid, and pharmaceutically acceptable esters, acids, and salts thereof.

90. The method of claim 1, wherein said IAPP-inhibiting compound is selected from the group consisting of the compounds 3-[2-(6,7-dimethoxy-1,2,3,4-tetrahydroisoquinolinyl)]-1-propanesulfonic acid, and pharmaceutically acceptable esters, acids, and salts thereof.

91. The method of claim 1, wherein said IAPP-inhibiting compound is selected from the group consisting of the compounds 3-[2-(6-methoxy-1,2,3,4-tetrahydroisoquinolinyl)]-1-propanesulfonic acid, and pharmaceutically acceptable esters, acids, and salts thereof.

92. The method of claim 1, wherein said IAPP-inhibiting compound is selected from the group consisting of the compounds 2-(2sulfobenzoyl)-1,2,3,4-tetrahydroisoquinoline, and pharmaceutically acceptable esters, acids, and salts thereof.

93. The method of claim 1, wherein said IAPP-inhibiting compound is selected from the group consisting of the compounds 2-(2-sulfobenzyl)-1,2,3,4-tetrahydroisoquinoline, and pharmaceutically acceptable esters, acids, and salts thereof.

94. The method of claim 1, wherein said IAPP-inhibiting compound is selected from the group consisting of the compounds 1,2,3,4-tetrahydroisoquinoline, and pharmaceutically acceptable esters, acids, and salts thereof.

95. The method of claim 1, wherein said IAPP-inhibiting compound is selected from the group consisting of the compounds 3-[2-(3-carboxy-1,2,3,4-tetrahydroisoquinolinyl)]-1-propanesulfonic acid, and pharmaceutically acceptable esters, acids, and salts thereof.

96. The method of claim 1, wherein said IAPP-inhibiting compound is selected from the group consisting of the compounds N-methyl-N-phenyl-3-[2-(1,2,3,4-tetrahydroisoquinolinyl)]-1-propanesulfonamide, and pharmaceutically acceptable esters, acids, and salts thereof.

97. The method of claim 1, wherein said IAPP-inhibiting compound is selected from the group consisting of the compounds 4-[2-(1,2,3,4-tetrahydroisoquinolinyl)]-1-butanesulfonic acid, and pharmaceutically acceptable esters, acids, and salts thereof.

98. The method of claim 1, wherein said IAPP-inhibiting compound is selected from the group consisting of the compounds 4-[2-(6,7-dimethoxy-1,2,3,4-tetrahydroisoquinolinyl)]-1-butanesulfonic acid, and pharmaceutically acceptable esters, acids, and salts thereof.

99. The method of claim 1, wherein said IAPP-inhibiting compound is selected from the group consisting of the compounds 4-[2-(6methoxy-1,2,3,4-tetrahydroisoquinolinyl)]-1-butanesulfonic acid, and pharmaceutically acceptable csters, acids, and salts thereof.

100. The method of claim 1, wherein said IAPP-inhibiting compound is selected from the group consisting of the compounds 3-[2-(1,2,3,4-tetrahydroisoquinolinyl)]-1-propylthiophosphonic acid, and pharmaceutically acceptable esters, acids, and salts thereof.

101. The method of claim 1, wherein said IAPP-inhibiting compound is selected from the group consisting of the compounds 3-[2-(6-methoxy-1,2,3,4-tetrahydroisoquinolinyl)]-1-propanesulfonic acid, and pharmaceutically acceptable esters, acids, and salts thereof.

102. The method of claim 1, wherein said IAPP-inhibiting compound is selected from the group consisting of the compounds 3-[2-(8-methoxy-1,2,3,4-tetrahydroisoquinolinyl)]-1-propanesulfonic acid, and phamaceutically acceptable esters, acids, and salts thereof.

103. The method of claim 1, wherein said IAPP-inhibiting compound is selected from the group consisting of the compounds 1,2,3,4-tetrahydro-8-isoquinolinesulfonic acid, and pharmaceutically acceptable esters, acids, and salts thereof.

104. The method of claim 1, wherein said IAPP-inhibiting compound is selected from the group consisting of the compounds 3-[2-(6-dimethylamino-1,2,3,4-tetrahydroisoquinolinyl)]-1-propanesulfonic acid, and pharmaceutically acceptable esters, acids, and salts thereof.

105. The method of claim 1, wherein said IAPP-inhibiting compound is selected from the group consisting of the compounds 3-[2-(6-chloro-1,2,3,4-tetrahydroisoquinolinyl)]-1-propanesulfonic acid, and pharmaceutically acceptable estrs, acids, and salts thereof.

106. The method of claim 1, wherein said IAPP-inhibiting compound is selected from the group consisting of the compounds 4-[2-(1,2,3,4tetrahydroisoquinolinyl)]-1-butanesulfonic acid, and pharmaceutically acceptable esters, acids, and salts thereof.

107. The method of claim 1, wherein said IAPP-inhibiting compound is selected from the group consisting of the compounds 1,2,3,4-tetrahydro-5-isoquinolinesulfonic acid, and pharmaceutically acceptable esters, acids, and salts thereof.

108. The method of claim 1, wherein said IAPP-inhibiting compound is selected from the group consisting of the compounds 1-sulfopropyl-2-[2-(1,2,3,4-tetrahydroisoquinolinyl)methyl]-4,5-dihydroimidazole, and pharmaceutically acceptable esters, acids, and salts thereof.

109. The method of claim 1, wherein said IAPP-inhibiting compound is selected from the group consisting of the compounds 3-[7-methoxy-2-(1,2,3,4-tetrahydroisoquinolinyl)]propylphosphonic acid, and pharmaceutically acceptable esters, acids, and salts thereof.

110. The method of claim 1, wherein said IAPP-inhibiting compound is selected from the group consisting of the compouads 3-[6-methoxy-2-(1,2,3,4-tetrahydroisoquinolinyl)]propylphosphonic acid, and pharmaceutically acceptable esters, acids, and salts threof.

111. The method of claim 1, wherein said IAPP-inhibiting compound is selected from the group consisting of the compounds 3-[8-methoxy-2-(1,2,3,4-tetrahydroisoquinolinyl)]propylphosphonic acid, and pharmaceutically acceptable esters, acids, and salts thereof.

112. The method of claim 1, wherein said IAPP-inhibiting compound is selected from the group consisting of the compounds 3-[2-(3-methoxycarbonyl-1,2,3,4-tetrahydroisoquinolinyl)]propylphosphonic acid, and pharmaceutically acceptable esters, acids, and salts thereof.

113. The method of claim 1, wherein said IAPP-inhibiting compound is selected from the group consisting of the compounds 3-[6-methoxy-2-(1,2,3,4-tetrahydroisoquinolinyl)]propylphosphonic acid, and pharmaceutically acceptable esters, acids, and salts thereof.

114. The method of claim 1, wherein said IAPP-inhibiting compound is selected from the group consisting of the compounds 3-[7-methoxy-2-(1,2,3,4-tetrahydroisoquinolinyl)]propylphosphonic acid, and pharmaceutically acceptable esters, acids, and salts thereof.

115. The method of claim 1, wherein said IAPP-inhibiting compound is selected from the group consisting of the compounds N-phosphonoacetyl-6-methoxy-1,2,3,4-tetrahydroisoquinoline, and pharmaceutically acceptable esters, acids, and salts thereof.

116. The method of claim 1, wherein said IAPP-inhibiting compound is selected from the group consisting of the compounds 6-methoxy-1,2,3,4-tetrahydroisoquinoline, and pharmaceutically acceptable esters, acids, and salts thereof.

117. The method of claim 1, wherein said IAPP-inhibiting compound is selected from the group consisting of the compounds N-sulfoacetyl-1,2,3,4-tetrahydroisoquinoline, and pharmaceutically acceptable esters, acids, and salts thereof.

118. The method of claim 1, wherein said IAPP-inhibiting compound is selected from the group consisting of the compounds N-ethyl-1,2,3,4-tetrahydroisoquinoline, and pharmaceutically acceptable esters, acids, and salts thereof.

119. The method of claim 1, wherein said IAPP-inhibiting compound is selected from the group consisting of the compounds N-propyl-1,2,3,4-tetrahydroisoquinoline, and pharmaceutically acceptable esters, acids, and salts thereof.

120. The method of claim 1, wherein said IAPP-inhibiting compound is selected from the group consisting of the compounds N-propyl-6-methoxy-1,2,3,4-tetrahydroisoquinoline, and pharmaceutically acceptable esters, acids, and salts thereof.

121. The method of claim 1, wherein said IAPP-inhibiting compound is selected from the group consisting of the compounds 5-[(1,2,3,4-tetrahydroisoquinol-2-yl)methyl]isoxazol-3-ol, and pharmaceutically acceptable esters, acids, and salts thereof.

122. The method of claim 1, wherein said IAPP-inhibiting compound is selected from the group consisting of the compounds 5-[(6-methoxy-1,2,3,4-tetrahydroisoquinol-2-yl)methyl]isoxazol-3-ol, and pharmaceutically acceptable esters, acids, and salts thereof.

123. The method of claim 1, wherein said IAPP-inhibiting compound is selected from the group consisting of the componnds (±)-laudanosoline, and pharmaceutically acceptable esters, acids, and salts thereof.

124. The method of claim 1, wherein said IAPP-inhibiting compound is selected from the group consisting of the compounds (−)-1-[5-chloro-2-(methylamino)phenyl]-1,2,3,4-tetrahydroisoquinoline (−)-tartrate, and pharmaceutically acceptable esters, acids, and salts thereof.

125. The method of claim 1, wherein said IAPP-inhibiting compound is selected from the group consisting of the compounds (S)-(−)-(1,2,3,4-tetrahydro-3-isoquiolinecarboxylic acid, and pharmaceutically acceptable esters, acids, and salts thereof.

126. The method of claim 1, wherein said IAPP-inhibiting compound is selected from the group consisting of the compounds tetrahydropapaveroline hydrobromide (norlaudanosoline hydrobromide), and pharmaceutically acceptable esters, acids, and salts thereof.

127. The method of claim 1, wherein said IAPP-inhibiting compound is selected from the group consisting of the compounds 3-phenyl-5-[2-(1,2,3,4-tetrahydroisoquinolyl)methyl]isoxazole, and pharmaceutically acceptable esters, acids, and salts thereof.

128. The method of claim 1, wherein said IAPP-inhibiting compound is selected from the group consisting of the compounds 3-methyl-5-[2-(1,2,3,4-tetrahydroisoquiolyl)methyl]isoxazole, and pharmaceutically acceptable esters, acids, and salts thereof.

129. The method of claim 1, wherein said IAPP-inhibiting compound is selected from the group consisting of the compounds 5-[2-(1,2,3,4-tetrahydroisoquinolyl)methyl]isoxazole-3-carboxylic acid, and pharmaceutically acceptable esters, acids, and salts thereof.

130. The method of claim 1, wherein said IAPP-inhibiting compound is selected from the group consisting of the compounds 5-phenyl-3-[2-(1,2,3,4-tetrahydroisoquinolinyl)methyl]isoxazole, and pharmaceutically acceptable esters, acids, and salts thereof.

131. The method of claim 1, wherein said IAPP-inhibiting compound is selected from the group consisting of the compounds 3-[2-(1,2,3,4-tetrahydroisoquinolyl)methyl]isoxazole-5-carboxylic acid, and pharmaceutically acceptable esters, acids, and salts thereof.

132. The method of claim 1, wherein said IAPP-inhibiting compound is selected from the group consisting of the compounds (2S)-2-amino-2-[3-(2-1,2,3,4-tetrahydroisoquinolylmethyl)isoxazol-5-yl]acetic acid, and pharmaceutically acceptable esters, acids, and salts thereof.

133. The method of claim 1, wherein said IAPP-inhibiting compound is selected from the group consisting of the compounds 3-[2-(1,2,3,4-tetrahydroisoquinolyl)methyl]isoxazole-5-L-alanine, and pharmaceutically acceptable esters, acids, and salts thereof.

134. The method of claim 1, wherein said IAPP-inhibiting compound is selected from the group consisting of the compounds 4-[2-(1,2,3,4-tetrahydroisoquinolyl)methyl]-L-phenylalanine, and pharmaceutically acceptable esters, acids, and salts thereof.

135. The method of claim 1, wherein said IAPP-inhibiting compound is selected from the group consisting of the compounds 5-[2-(1,2,3,4-tetrahydroisoquinolyl)methyl)-

136. The method of claim 1, wherein said IAPP-inhibiting compound is selected from the group consisting of the compounds 5-(1,2,3,4-tetrahydroisoquinol-6-yl)-1H-1,2,3,4-tetrazole, and pharmaceutically acceptable esters, acids, and salts thereof.

137. The method of claim 1, wherein said IAPP-inhibiting compound is selected from the group consisting of the compounds 5-[6-(1,2,3,4-tetrahydroisoquinolyl)methyl]-1H-1,2,3,4-tetrazole, and pharmaceutically acceptable esters, acids, and salts thereof.

138. The method of claim 1, wherein said IAPP-inhibiting compound is selected from the group consisting of the compounds 5-{2-[6-(1,2,3,4-tetrahydroisoquinolyl)]ethyl}-1H-1,2,3,4-tetrazole, and pharmaceutically acceptable esters, acids, and salts thereof.

139. The method of claim 1, wherein said IAPP-inhibiting compound is selected from the group consisting of the compounds 5-(1,2,3,4-tetrahydroisoquinol-7-yl)-1H-1,2,3,4-tetrazole, and pharmaceutically acceptable esters, acids, and salts thereof.

140. The method of claim 1, wherein said IAPP-inhibiting compound is selected from the group consisting of the compounds 5-[7-(1,2,3,4-tetrahydroisoquinolyl)methl]-1H-1,2,3,4-tetrazole, and pharmaceutically acceptable esters, acids, and salts thereof.

141. The method of claim 1, wherein said IAPP-inhibiting compound is selected from the group consisting of the compounds 5-{2-[7-(1,2,3,4-tetrahydroisoquinolyl)]ethyl}-1H-1,2,3,4-tetrazole, and pharmaceutically acceptable esters, acids, and salts thereof.

142. The method of claim 1, wherein said IAPP-inhibiting compound is selected from the group consisting of the compounds 6-methoxy-1,2,3,4-tetrahydroisoquinoline, and pharmaceutically acceptable esters, acids, and salts thereof.

143. The method of claim 1, wherein said IAPP-inhibiting compound is selected from the group consisting of the compounds 7-methoxy-1,2,3,4-tetrahydroisoquinoline, and pharmaceutically acceptable ester, acids, and salts thereof.

144. The method of claim 1, wherein said IAPP-inhibiting compound is selected from the group consisting of the compounds 6,7-dimethoxy-1,2,3,4-tetrahydroisoquinoline, and pharmaceutically acceptable esters, acids, and salts thereof.

145. The method of claim 1, wherein said IAPP-inhibiting compound is selected from the group consisting of the compounds 1,2,3,4-tetrahydroisoquinoline-6-carbonitrile, and pharmaceutically acceptable esters, acids, and salts thereof.

146. The method of claim 1, wherein said IAPP-inhibiting compound is selected from the group consisting of the compounds 1,2,3,4-tetrahydroisoquinoline-7-carbonitrile, and pharmaceutically acceptable esters, acids, a salts thereof.

147. The method of claim 1, wherein said IAPP-inhibiting compound is selected from the group consisting of the compounds 6-amino-1,2,3,4-tetrahydroisoquinoline, and the pharmaceutically acceptable esters, acids, and salts thereof.

148. The method of claim 1, wherein said IAPP-inhibiting compound is selected from the group consisting of the compounds 7-amino-1,2,3,4-tetrahydroisoquinoline, and pharmaceutically acceptable esters, acids, and salts thereof.

149. The method of claim 1, wherein said IAPP-inhibiting compound is selected from the group consisting of the compounds 7-(3,4,5-trimethoxybenzoyl)amino-1,2,3,4-tetrahydroisoquinoline, and pharmaceutically acceptable esters, acids, and salts thereof.

150. The method of claim 1, wherein said IAPP-inhibiting compound is selected from the group consisting of the compounds 7-β-D-glucopyranosyl-6-methoxy-1,2,3,4-tetrahydroisoquinoline, and pharmaceutically acceptable esters, acids, and salts thereof.

151. The method of claim 1, wherein said IAPP-inhibiting compound is selected from the group consisting of the compounds 6-β-D-glucopyranosyl-7-methoxy-1,2,3,4-tetrahydroisoquinoline, and pharmaceutically acceptable esters, acids, and salts thereof.

152. The method of claim 1, wherein said IAPP-inhibiting compound is selected from the group consisting of the compounds (1,2,3,4-tetrahydroisoquinol-1-yl)phosphonic acid, and pharmaceutically acceptable esters, acids, and salts thereof.

153. The method of claim 1, wherein said IAPP-inhibiting compound is selected from the group consisting of the compounds 5,6,7,8-tetrahydro-2H-1,3-dioxoleno[4,5-g]isoquinoline, and pharmaceutically acceptable esters, acids, and salts thereof.

154. The method of claim 1, wherein said IAPP-inhibiting compound is selected from the group consisting of the compounds 1,2,3,4-tetrahydrobenzo[g]isoquinoline, and pharmaceutically acceptable esters, acids, and salts thereof.

155. The method of claim 1, wherein said IAPP-inhibiting compound is selected from the group consisting of the compounds (1,2,3,4-tetrahydroisoquinol-7-ylsulfonyl)aminobenzene, and pharmaceutically acceptable esters, acids, and salts thereof.

156. The method of claim 1, wherein said IAPP-inhibiting compound is selected from the group consisting of the compounds 1-[(1,2,3,4-tetrahydroisoquinol-7-ylsulfonyl)amino]-3,4-dichlorobenzene, and pharmaceutically acceptable esters, acids, and salts thereof.

157. The method of claim 1, wherein said IAPP-inhibiting compound is selected from the group consisting of the compounds 7-(2,2,2-trifluoroacetyl)-1,2,3,4-tetrahydroisoquinoline, and pharmaceutically acceptable esters, acids, and salts thereof.

158. The method of claim 1, wherein said IAPP-inhibiting compound is selected from the group consisting of the compounds 7-benzyl-1,2,3,4-tetrahydroisoquinoline, and pharmaceutically acceptable esters, acids, and salts thereof.

159. The method of claim 1, wherein said IAPP-inhibiting compound is selected from the group consisting of the compounds 7-benzoyl-1,2,3,4-tetrahydroisoquinoline, and pharmaceutically acceptable esters, acids, and salts thereof.

160. The method of claim 1, wherein said IAPP-inhibiting compound is selected from the group consisting of the compounds 7-acetyl-1,2,3,4-tetrahydroisoquinoline, and pharmaceutically acceptable esters, acids, and salts thereof.

161. The method of claim 1, wherein said IAPP-inhibiting compound is selected from the group consisting of the compounds 1,2,3,4-tetrahydroisoquinoline-7-carboxylic acid, and pharmaceutically acceptable esters, acids, and salts thereof.

162. The method of claim 1, wherein said IAPP-inhibiting compound is selected from the group consisting of the compounds 1,2,3,4-tetrahydroisoquinoline-7-carboxamide, and pharmaceutically acceptable esters, acids, and salts thereof.

163. The method of claim 1, wherein said IAPP-inhibiting compound is selected from the group consisting of the compounds 7-aminomethyl-1,2,3,4-tetrahydroisoquinoline, and pharmaceutically acceptable esters, acids, and salts thereof.

164. The method of claim 1, wherein said IAPP-inhibiting compound is selected from the group consisting of the compounds 7-hydroxymethyl-1,2,3,4-tetrahydroisoquinoline, and pharmaceutically acceptable esters, acids, and salts thereof.

165. The method of claim 1, wherein said IAPP-inhibiting compound is selected from the group consisting of the compounds 7-methyl-1,2,3,4-tetrahydroisoquinoline, and pharmaceutically acceptable esters, acids, and salts thereof.

166. The method of claim 1, wherein said IAPP-inhibiting compound is selected from the group consisting of the compounds 7-hydroxy-1,2,3,4-tetrahydroisoquinoline, and pharmaceutically acceptable esters, acids, and salts thereof.

167. The method of claim 1, wherein said IAPP-inhibiting compound is selected from the group consisting of the compounds 7-(methanesulfonyl)amino-1,2,3,4-tetrahydroisoquinoline, and pharmaceutically acceptable esters, acids, and salts thereof.

168. The method of claim 1, wherein said IAPP-inhibiting compound is selected from the group consisting of the compounds 7-(methanesulfonyl)aminomethyl-1,2,3,4-tetrahydroisoquinoline, and pharmaceutically acceptable esters, acids, and salts thereof.

169. The method of claim 1, wherein said IAPP-inhibiting compound is selected from the group consisting of the compounds 7-nitro-1,2,3,4-tetrahydroisoquinoline, and pharmaceutically acceptable esters, acids, and salts tbereof.

170. The method of claim 1, wherein said IAPP-inhibiting compound is selected from the group consisting of the compounds 1,2,3,4-tetrahydroisoquinoline-7-sulfonamide, and pharmaceutically acceptable esters, acids, and salts thereof.

171. The method of claim 1, wherein said IAPP-inhibiting compound is selected from the group consisting of the compounds 7-trifluoromethyl-1,2,3,4-tetrahydroisoquinoline, and pharmaceutically acceptable esters, acids, and salts thereof.

172. The method of claim 1, wherein said IAPP-inhibiting compound is selected from the group consisting of the compounds 7-methylthio-1,2,3,4-tetrahydroisoquinoline, and pharmaceutically acceptable esters, acids, and salts thereof.

* * * * *

UNITED STATES PATENT AND TRADEMARK OFFICE
CERTIFICATE OF CORRECTION

PATENT NO. : 6,562,836 B1
DATED : May 13, 2003
INVENTOR(S) : Walter A. Szarek et al.

It is certified that error appears in the above-identified patent and that said Letters Patent is hereby corrected as shown below:

Column 17,
Line 48, "compowuds" should read -- compounds --.

Column 22,
Line 7, "componnds" should read -- compounds --.

Signed and Sealed this

Sixth Day of April, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,562,836 B1
DATED : May 13, 2003
INVENTOR(S) : Walter A. Szarek et al.

It is certified that error appears in the above-identified patent and that said Letters Patent is hereby corrected as shown below:

Column 17,
Line 48, "compowuds" should read -- compounds --.

Column 22,
Line 7, "componnds" should read -- compounds --.

Signed and Sealed this

Fifth Day of October, 2004

JON W. DUDAS
*Director of the United States Patent and Trademark Office*

UNITED STATES PATENT AND TRADEMARK OFFICE
CERTIFICATE OF CORRECTION

PATENT NO. : 6,562,836 B1
DATED : May 13, 2003
INVENTOR(S) : Walter A. Szarek et al.

It is certified that error appears in the above-identified patent and that said Letters Patent is hereby corrected as shown below:

Title page,
Item [73], Assignee, "Queen's University of Kingston" should read -- Queen's University at Kingston -- and please add:
-- Neurochem (Internationl) Limited
  Walchwil (CH) --.

Signed and Sealed this

Twentieth Day of September, 2005

JON W. DUDAS
*Director of the United States Patent and Trademark Office*